(12) United States Patent
Sun et al.

(10) Patent No.: US 6,808,611 B2
(45) Date of Patent: Oct. 26, 2004

(54) METHODS IN ELECTROANALYTICAL TECHNIQUES TO ANALYZE ORGANIC COMPONENTS IN PLATING BATHS

(75) Inventors: Zhi-wen Sun, San Jose, CA (US); Chunman Yu, Sunnyvale, CA (US); Brian Metzger, San Jose, CA (US); David W. Nguyen, San Jose, CA (US); Girish Dixit, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 290 days.

(21) Appl. No.: 10/187,734

(22) Filed: Jun. 27, 2002

(65) Prior Publication Data

US 2004/0000484 A1 Jan. 1, 2004

(51) Int. Cl.[7] .................. C25D 21/00; G01N 27/26

(52) U.S. Cl. .................. 205/81; 204/400; 204/434; 205/775; 205/787

(58) Field of Search .................. 205/81, 775, 787; 204/400, 434

(56) References Cited

U.S. PATENT DOCUMENTS

| | | | |
|---|---|---|---|
| 4,132,605 A | 1/1979 | Tench et al. | 204/1 T |
| 4,321,322 A | 3/1982 | Ahnell | 435/34 |
| 4,376,569 A | 3/1983 | Barltrop et al. | 350/357 |
| 4,479,852 A | 10/1984 | Bindra et al. | 204/1 T |
| 4,514,265 A | 4/1985 | Rao et al. | 204/15 |
| 4,725,339 A | 2/1988 | Bindra et al. | 204/1 T |
| 5,192,403 A | 3/1993 | Chang et al. | 204/153.1 |
| 5,196,096 A | 3/1993 | Chang et al. | 204/153.1 |
| 5,223,118 A | 6/1993 | Sonnenberg et al. | 205/81 |

(List continued on next page.)

OTHER PUBLICATIONS

Tench, et al. "A New Voltammetric Stripping Method Applied to the Determination of the Brightener Concentration in Copper Pyrophosphate Plating Baths", Journal of the Electrochemical Society, vol. 125, pp 194–198, no date given.

Tench, et al. "Cyclic Pulse Voltammetric Stripping Analysis of Acid Copper Plating Baths", Journal of Electrochemical Society, Apr. 1985, pp 831–833.

Haak, et al. "Cyclic Voltammetric Stripping Analysis of Acid Copper Sulfate Plating Baths", Plating and Surface Finishin, Apr. 1981, pp 52–55.

Moffatt, et al. "Superconformal Electrodiposition of Copper in 500–90 nm Features", Journal of the Electrochemical Society, 147 (12) 4524–4535 (2000) no month given.

Kelly, et al. "Leveling and Microstructural Effects of Additives for Copper Electrodeposition", Journal of the Electrochemical Society, 146 (7)2540–2545 (1999) no month given.

Primary Examiner—Robert R. Koehler
(74) Attorney, Agent, or Firm—Moser, Patterson & Sheridan

(57) ABSTRACT

Embodiments of the invention provide an electro-analytical method for determining the concentration of an organic additive in an acidic or basic metal plating bath using an organic chemical analyzer. The method includes preparing a supporting-electrolyte solution, preparing a testing solution including the supporting-electrolyte solution and a standard solution, measuring an electrochemical response of the supporting-electrolyte solution using the organic chemical analyzer, and implementing an electro-analytical technique to determine the concentration of the organic additive in the plating bath from the electrochemical response measurements. The method is performed for independently analyzing one organic additive component in a plating bath containing multi-component organic additives, regardless of knowledge of the concentration of other organic additives and with minimal interference among organic additives.

35 Claims, 7 Drawing Sheets

U.S. PATENT DOCUMENTS

| | | | |
|---|---|---|---|
| 5,389,215 A | 2/1995 | Horiuchi et al. | 204/153.1 |
| 5,389,546 A | 2/1995 | Becket | 436/51 |
| 5,635,043 A | 6/1997 | Tur'yan et al. | 204/412 |
| 5,755,954 A | 5/1998 | Ludwig et al. | 205/794 |
| 5,908,540 A | 6/1999 | Fanti | 204/242 |
| 5,972,192 A | 10/1999 | Dubin et al. | 205/101 |
| 6,024,857 A | 2/2000 | Reid | 205/123 |
| 6,113,759 A | 9/2000 | Uzoh | 204/285 |
| 6,113,771 A | 9/2000 | Landau et al. | 205/123 |
| 6,140,241 A | 10/2000 | Shue et al. | 438/692 |
| 6,176,992 B1 | 1/2001 | Talich | 205/87 |
| 6,224,737 B1 | 5/2001 | Tsai et al. | 205/123 |
| 6,280,602 B1 | 8/2001 | Robertson | 205/775 |

—♦— NO LEVELER

—●— 0.5 ml/L LEVELER

- 5S
- 6A5S
- 5S5L

- 6A5S
- 5S
- 6A5S5L
- 5S5L

METHODS IN ELECTROANALYTICAL TECHNIQUES TO ANALYZE ORGANIC COMPONENTS IN PLATING BATHS

BACKGROUND OF THE INVENTION

1. Field of the Invention

Embodiments of the invention generally relate to deposition of a metal layer onto a wafer/substrate. Particularly, the invention relates to electro-chemical deposition systems, integrated with electrolyte analyzing modules, for forming a metal layer on a wafer/substrate. More particularly, the invention relates to a method for measuring the concentration of components, including additives in a plating solution useful in electrochemical deposition systems.

2. Description of the Related Art

The semiconductor industry's progress in multilevel metallization of topographical interconnect features with diverse pattern densities commonly used in the manufacture of high performance very large scale integration (VLSI) and ultra large-scale integration (ULSI) devices has pushed semiconductor performance ever faster. As the fringes of circuit technology are pressed, the shrinking dimensions of the interconnects in sub-quarter micron and smaller features for the next generation of VLSI and ULSI technologies has placed additional demands on the processing capabilities. The multilevel interconnects that lie at the heart of semiconductor technology require precise processing of high aspect ratio features, such as vias, contacts, lines, and other interconnects. Reliable formation of these interconnects is important to VLSI and ULSI success and to the continued effort to increase circuit density and quality of individual substrates and die.

Electro-chemical plating (ECP), originally used in other industries, has been applied in the semiconductor industry as a deposition technique for filling sub-quarter micron features because of its ability to grow the deposited material, such as copper, on a conductive surface and fill even high aspect ratio features substantially free of voids. Typically, a metallic diffusion barrier layer is deposited over a feature surface, followed by the deposition of a conductive metal seed layer. Then, a conductive metal is electro-chemically plated over the seed layer to fill the structure/feature. Finally, the surface of the features are planarized, such as by chemical mechanical polishing (CMP), to define a conductive interconnect feature.

Copper has become the desired metal for semiconductor device fabrication, because of its lower resistivities and significantly higher electromigration resistance as compared to aluminum, and good thermal conductivity. Copper electrochemical plating systems have been developed for semiconductor fabrication of advanced interconnect structures. Typically, copper ECP uses a plating bath/electrolyte including positively charged copper ions in contact with a negatively charged substrate, as a source of electrons, to plate out the copper on the charged substrate.

All ECP electrolytes have both inorganic and organic compounds at low concentrations. Typical inorganics include copper sulfate ($CuSO_4$), sulfuric acid ($H_2SO_4$), and trace amounts of chloride ($Cl^-$) ions. Typical organics include accelerators, suppressors, and levelers. An accelerator is sometimes called a brightener or anti-suppressor. A suppressor may be a surfactant or wetting agent, and is sometimes called a carrier. A leveler is also called a grain refiner or an over-plate inhibitor.

Although simple in principle, copper plating relies in practice on the use of proper additives in the electrolyte to determine the properties of the copper being deposited. Because of depletion, analysis of the processing additives is required periodically during the plating process. If the concentrations change, or if the additive components get out of balance, the quality of the plated copper deteriorates. Monitoring and control of inorganic and organic additives by chemical analyzers are very important, especially as the technological demands on the copper become more stringent.

Additive control in copper plating is a major scientific and technological challenge. The electrochemical signals, such as electric potential and current, are functions of all the organic additives added, and require detailed analyses to determine the composition of the electrolyte to ensure proper proportions of the components. Conventional analysis is performed by extracting a sample of electrolyte from a test port followed by transferring the sample to a remote chemical analyzer. The electrolyte composition is then adjusted according to the results of the analysis. The analysis must be performed frequently because the concentrations of the various chemicals are in constant flux.

Organic chemical analyzers implementing different electro-analytical principles such as CVS (Cyclic Voltammetric Stripping), CPVS (Cyclic Pulse Voltammetric stripping), and PCGA (Pulsed Cyclic Galvanostatic Analysis) are widely used for the analysis of organic additive concentration in metal plating baths. The organic chemical analyzer is typically coupled to a metal plating apparatus, such as an electrochemical plating (ECP) apparatus for depositing metal films on semiconductor devices. These electro-analytical principles are based on high sensitivity of electrochemical responses, such as over-potential or current, of metal plating processes toward trace amounts of organic additives inside a plating cell/container of the organic chemical analyzer to provide bath additive analysis.

Despite claims that organic chemical analysis performed by various electro-analytical principles can be used as monitoring tools and the availability of CVS, PCGA, and CPVS instruments, many serious questions about additive analysis still arise. This is because in commercial production plating baths, all additives co-exist and can adsorb on the surface of an electrode inside the organic chemical analyzer to affect the quality of the plated metals, resulting in so-called interference effect or matrix effect.

In the implementation of CVS, PCGA, and CPVS principles, different supporting-electrolyte solutions are thus prepared inside the plating cell of the organic chemical analyzer for measuring electrochemical responses to minimize or eliminate the interference effect coming from one type of organic additive on the electrode surface. For example, excess amounts of suppressor solution are mixed with an inorganic virgin make-up solution to make up a supporting-electrolyte solution for analyzing the concentration of an accelerator type additive by a Modified Linear Approximation Technique (MLAT). In addition, a Dilution Titration (DT) method with virgin make-up solutions (VMS) as the supporting-electrolyte solution has been used to analyze the concentration of a suppressor. The VMS solution includes at least three inorganic components, such as charged cations of the metal to be plated, charged anions, an acid or base for adjusting pH and bath electrical resistance, and combinations thereof. In many cases, however, inorganic VMS is not sufficient as the supporting-electrolyte solution, and the analysis accuracy and precision suffer because other types of organic additives in the solution to be tested still exert significant interference to the dependence of the electrochemical responses on the organic additive to be analyzed.

In addition, the foregoing analytical methods are time consuming and limited in terms of the number of analyses being performed and analysis must be repeated continuously to obtain any degree of control, because concentration of organics is changing continuously during the plating operation. For example, the CVS methods cannot measure all different types of organic components independently. Two or more of the organic components have to be analyzed independently of each other prior to finding the information on the concentrations of these two components fed into the analyses of the third component to get reliable and accurate analyses on the concentration of the third component. This severely limited the user's capability to analyze the concentration of the third component at any desired moment.

For example, in determining the concentration of a leveler, knowledge of the concentrations of all other co-existing components is required before the concentration of the leveler can be determined. Thus, it is difficult to minimize or even eliminate the interference effect to obtain reliable analysis results.

Therefore, a need exists to provide methods for real-time independent analysis of each electrolyte component in a processing system integrated with one or more chemical analyzers.

SUMMARY OF THE INVENTION

Embodiments of the invention provide an electroanalytical method for determining the concentration of an organic additive in an acidic or basic metal plating bath using an organic chemical analyzer. The method includes preparing a supporting-electrolyte solution, preparing a testing solution, measuring an electrochemical response of the supporting-electrolyte solution and the testing solution using the organic chemical analyzer, and implementing an electroanalytical technique to determine the concentration of the organic additive in the plating bath from the electrochemical response measurements. The method is performed for independently analyzing one organic additive component in a plating bath containing multi-component organic additives.

In one embodiment, a method for determining the concentration of an accelerator in an unknown plating bath using an organic chemical analyzer is provided, regardless of the knowledge of the concentration of a suppressor, a leveler, or other organic additives, and with minimal interference among organic additives. The supporting-electrolyte solution for determining the accelerator concentration includes a virgin make-up solution, up to about 5 ml/L of the accelerator, brightener, or anti-suppressor, and between about 10 ml/L and about 60 ml/L of a suppressing agent of the plating bath. The testing solution for determining the accelerator concentration includes the supporting-electrolyte solution and a production solution having a dilution aliquot of the plating bath, and optionally at least one volume of a standard solution having known concentration of at least one organic additive for the plating bath.

In another embodiment, a method for determining the concentration of a suppressor in an unknown plating bath using an organic chemical analyzer is provided, regardless of the knowledge of the concentrations of an accelerator, a leveler, or other organic additives, and with minimal interference among organic additives. The supporting-electrolyte solution for determining the suppressor concentration includes a virgin make-up solution of all inorganic substances of the plating bath and up to about 0.5 ml/L of the suppressor, carrier, surfactant, or wetting agent of interest. The testing solution for determining the suppressor concentration includes the supporting-electrolyte solution and at least one volume of a standard solution having known concentration of at least one organic additive for the plating bath.

In another embodiment, a method for determining the concentration of a leveler in an unknown plating bath using an organic chemical analyzer is provided, regardless of the knowledge of the concentrations of an accelerator, a suppressor, or other organic additives, and with minimal interference among organic additives. The supporting-electrolyte solution for determining the leveler concentration includes a virgin make-up solution, up to about 60 ml/L of an accelerator, brightener, or anti-suppressor, and up to about 60 ml/L of a suppressor, carrier, surfactant, or wetting agent except the leveler, over-plate inhibitor, or grain refiner of interest. The testing solution for determining the leveler concentration includes the supporting-electrolyte solution and at least one volume of a standard solution having known concentration of at least one organic additive for the plating bath.

BRIEF DESCRIPTION OF THE DRAWINGS

So that the manner in which the features of the invention are attained and can be understood in detail, a more particular description of the invention, briefly summarized above, may be had by reference to the embodiments thereof, which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Figure 1:
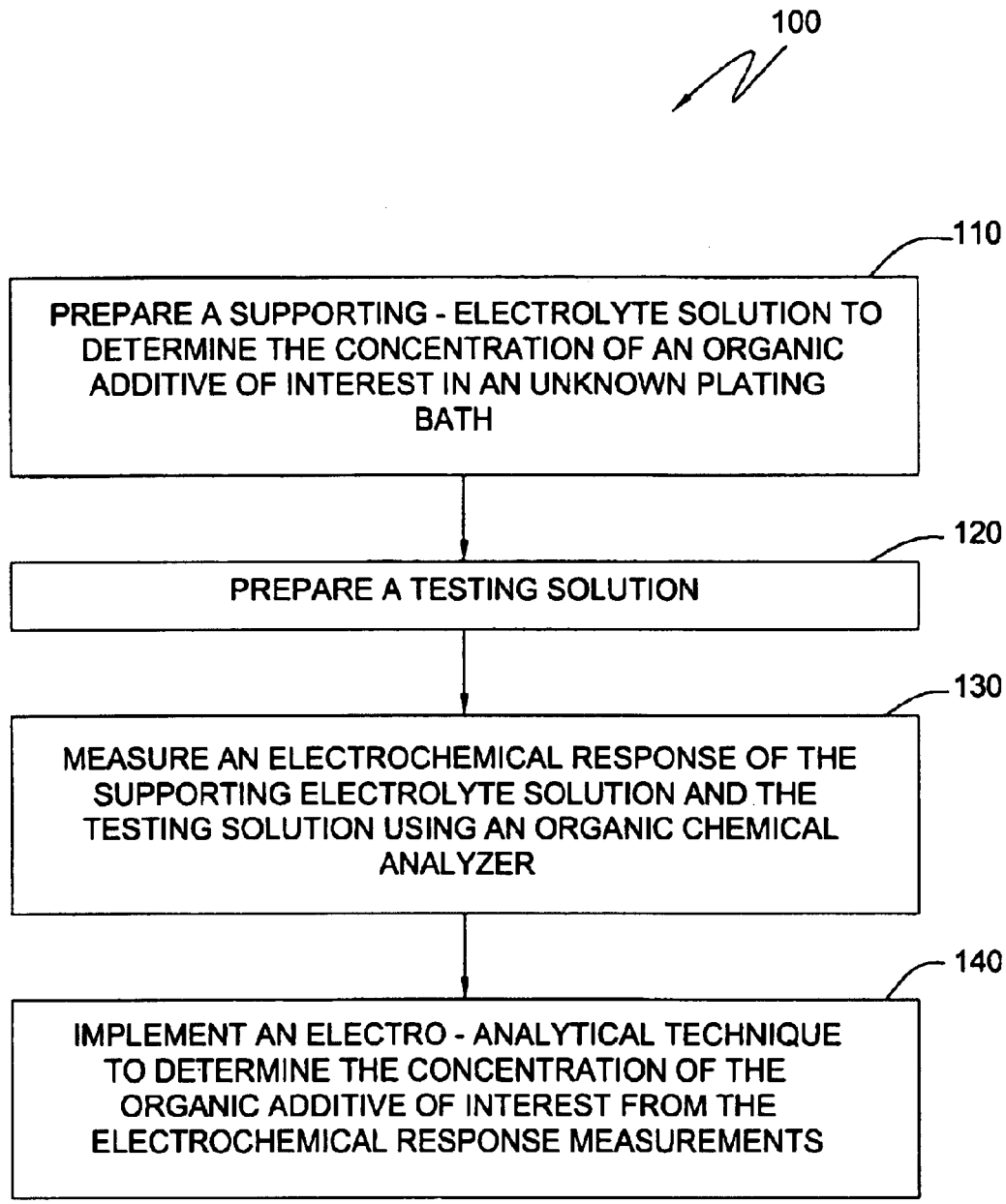
FIG. 1 is a flow diagram illustrating an exemplary electroanalytical method.

The words and phrases used herein should be given their ordinary and customary meaning by one skilled in the art unless otherwise further defined.

Embodiments of the invention include methods for determining the concentration of an organic additive of interest in an acidic or basic electro-chemical plating bath containing multiple organic additives. The methods are performed to analyze all organic components independently, regardless of the interference effect or matrix effect on the surface of an electrode, which is achieved by preparing proper supporting-electrolyte solutions in plating baths and implementing different electro-analytical techniques.

Electro-Chemical Deposition or Electro-Chemical Plating (ECP) should be broadly construed and includes, but is not limited to, deposition of a film carried out in a chemical solution or plating bath inside a plating cell/container having a cathode, an anode therein and induced by the passage of an electric current or chemical reduction of metal ions that are neutralized by the electrons supplied by a reducing agent in the bath. 3.

Interference Effect (or Matrix Effect) as defined herein refers to the effect of co-existing additives on an electro-chemical response of an additive under analysis. The electrochemical response signals such as electric potential, electric charges, and current are functions of all the organic additives involved.

In one embodiment, small concentrations of an accelerator are shown to be required as part of a supporting-electrolyte solution by implementing a MLAT technique together with an organic chemical analyzer. The concentration of the accelerator in an unknown plating bath can be determined in the presence of a supporting-electrolyte solution, which includes a virgin make-up solution (VMS), excess amounts of a suppressor and trace amounts of the accelerator such that interference effect on the accelerator from a leveler and the suppressor is at its minimal level. Virgin Make-Up Solution (VMS) as defined herein refers to a solution composed of only inorganic components or additives that are commonly used in a plating bath.

For example, the supporting-electrolyte solution for determining the accelerator concentration includes a VMS solution, up to about 5 ml/L of the accelerator, brightener, or anti-suppressor, and between about 10 ml/L and about 60 ml/L of a suppressing agent of the plating bath.

In another embodiment, the concentration of a suppressor in an unknown plating bath with minimal interference effect either from an accelerator or a leveler can be determined by including a VMS solution and trace amounts of the suppressor into a supporting-electrolyte solution and analyzing measured plating-response values by a DT technique in an organic chemical analyzer.

For example, the supporting-electrolyte solution for determining the suppressor concentration includes a VMS solution of all inorganic substances of the plating bath and up to about 0.5 ml/L of the suppressor, carrier, surfactant, or wetting agent of interest.

In another embodiment, the concentration of a leveler is independently analyzed without knowing the concentration of other organic additives in a plating bath. Such analysis is performed by a DT technique in the presence of a supporting-electrolyte solution including a VMS solution and excess amounts of a suppressor and an accelerator.

For example, the supporting-electrolyte solution for determining the leveler concentration includes a VMS solution, up to about 60 ml/L of an accelerator, brightener, or anti-suppressor, and up to about 60 ml/L of a suppressor, carrier, surfactant, or wetting agent except the leveler, over-plate inhibitor, or grain refiner of interest.

In another embodiment, by performing the electro-analytical methods provided herein, the concentrations of any of the three types of organic additives in a given plating bath is determined in real time either manually or automatically using an organic analyzer, coupled to an electro-chemical plating system, regardless of the knowledge of the other organic additives in the plating baths. Therefore, all three types of organic components can be independently analyzed. The analysis of a third organic component is done independently from the other two types of additives by combining the appropriate supporting-electrolyte solutions for each type of organic additives and the electro-analytical method used.

Supporting-Electrolyte Solution as used herein is defined as a solution needed for analyzing the composition of electroplating additives by a chemical analyzer. Inside a cell/container of a chemical analyzer, the most common supporting-electrolyte solution is a plating bath inorganic make-up solution called VMS (Virgin Make-Up). In addition, a chemical analyzer cell may further include a known volume of a testing solution which include a portion or a dilution of an unknown solution.

An accelerator (as defined herein also includes brightener or anti-suppressor) is an organic additive in a plating bath used to catalyze and speed-up the filling of vias and trenches. Accelerators are typically sulfur-containing molecules, such as those having sulfonic acid groups or disulfides, e.g., SPS (Bis-(sodium sulfopropyl)-disulfide) with the chemical formula of $NaSO_3(CH_2)_3S—S(CH_2)_3SO_3Na$.

A suppressor (as defined herein also includes a surfactant, wetting agent, or carrier) is an organic additive in a plating bath that suppresses Cu growth at the top edges of vias and trenches. Surfactants may be long chain polymers such as polyethylene glycol (PEG) or co-polymers of polyoxyethylene and polyoxypropylene having mean molecular weights greater than 1000.

A leveler (as defined herein also includes a grain refiner or over-plate inhibitor) is an organic additive in a plating bath that controls the grain size of the plated copper and inhibits copper over-plating above the top of the trench, a phenomenon called mushrooming. Levelers are usually high molecular weight polymers with amine ($—NH_3$) or amide ($—NH_2$) functional groups.

Electro-Analytical Techniques

Electro-analytical techniques of the invention include, but are not limited to, Modified Linear Approximation Technique (MLAT), Dilution Titration (DT), Response Curve (RC), and Quick Check (QC) techniques. These techniques can be refined and optimized for on-line monitoring of additive concentrations in plating baths together with an organic chemical analyzer, which measures plating responses of the plating baths.

The plating-responses as used herein include, but are not limited to, cathodic deposition rates, cathodic deposition charges, cathodic deposition area, anodic stripping rates, anodic stripping charges, anodic stripping area, electrical plating potentials between cathodic and reference electrodes, AC or DC currents, or differential currents, depending on the organic chemical analyzer used.

Cyclic Voltammetric Stripping (CVS) is a technique based on the principle of cyclic voltammetry and the rate of metal deposition during precisely controlled electroplating to be used for monitoring additive concentration in a plating bath. The potential of an inert rotating electrode is swept at a constant rate back and forth between negative and positive voltage limits.

The basis of CVS analysis is that the additives change the polarization of a metal deposition reaction and therefore affect the amounts of metal deposited in a linear potential sweep applied to an inert electrode in a plating bath. Inside a cyclic voltammetric stripper, a small amount of a metal from a sample testing solution is alternately electroplated onto the inert electrode and then stripped off by anodic dissolution. Therefore, stripping charges required to strip the metal are measured as plating-responses correlated to the deposition rate of the metal and are affected by the content and concentrations of the active additives in the plating bath.

The CVS stripping charges are also affected by various CVS conditions. CVS conditions typically include at least three different parameters, an electronic rotational speed of the inert rotating electrode presented as revolutions per minute (rpm), an electric potential scan rate as milivolts per second (mV/s) and a negative potential limit as milivolts (mV). Electrode potential as used herein includes, but is not limited to, the electrical voltage measured between the inert rotating electrode and a reference electrode inserted into the plating cell. A typical reference electrode is silver (Ag)/silver chloride (AgCl) reference electrode.

$A_r$ Values as used herein include, but are not limited to, the area under a stripping peak of a typical CVS voltammogram of a metal plating bath. $A_r$ value represents the stripping area (Ar) of anodic stripping charges measured as the total electrical charge in millicoulombs (millicoulombs= milliamperesxseconds) required to strip a plated metal material from a rotating inert electrode of a CVS stripper. $A_r$ values are typically measured for various plating baths/solutions and employed in various electro-analytical techniques to analyze additive levels in an electroplating bath/solution. For example, the stripping area ($A_r$) of anodic copper stripping charges is measured as integrated anodic currents in millicoulombs (mC) and correlates directly with the amount of cathodic copper deposited, and thus is a measurement of copper deposition rate.

Modified Linear Approximation Technique (MLAT) is a technique utilizing the anti-suppression property of an organic additive, such as an accelerator, to determine the concentration of the additive in an unknown plating bath. A MLAT electro-analytical technique is based on the linear relationship of plating response measurements as a function of organic additive concentrations, y=ax+b, where y is a plating response measurement and x is the concentration of an additive. The intercept "b" plating response measurement has to be determined in a supporting-electrolyte solution without the presence of the additive, i.e., x equals to zero. MLAT includes preparing a supporting-electrolyte solution, measuring an intercept plating response in the presence of the supporting-electrolyte solution, and performing plating responses of various solutions required and prepared for determining the concentration of an additive of interest in an unknown plating bath In general, the supporting-electrolyte solution includes VMS plus excess amount of a suppressing agent. For MLAT to work properly, dilution of the unknown plating bath with the supporting-electrolyte solution in testing solutions is needed because of the high sensitivity of the electrochemical responses toward trace amounts of additives. Diluting the plating bath with the VMS or supporting-electrolyte solution only reduces the effective additive concentration in the testing solutions in order to analyze additive concentration in the original unknown plating bath. The response curve is quite linear in the region of diluted additive concentrations. Because of the linear relationship, in other words, a constant slope "a" value, one can determine active additive concentration directly even without the use of a response curve. Once the additive concentration in the testing solutions are known, the concentration in the unknown plating bath can be calculated based on the known dilution factor.

Dilution Titration (DT) technique is an electro-analytical technique utilizing the effect of additive components that suppress or decrease the metal deposition rate and the effective concentrations occur only at very low concentrations, such as 5 ml/L or less, in order to analyze the concentration of the additive components in a unknown plating bath/solution. The DT technique includes preparing a supporting-electrolyte solution, preparing a dilution series of an unknown plating bath in the presence of the supporting-electrolyte solution, obtaining the results of a specific test-response, such as a CVS plating-response, and comparing plating responses of the dilution series of the unknown plating bath with a dilution series of an additive of interest at known concentrations to determine the concentration of the additive of interest in the unknown plating bath.

Sometimes, further dilution of the unknown solution is required such that effective additive concentrations in the unknown test series are quite low. When comparing at least two sets of the test-response results, an endpoint of a particular $A_r/A_{r0}$, where $A_{r0}$ stands for the $A_r$ value of only a supporting-electrolyte solution present inside a plating cell, is chosen to assume an approximately linear fit of the test-response curves, meaning the same degree of plating suppression for their response curves.

A RC electro-analytical technique includes preparing a supporting-electrolyte solution and performing plating responses of small increments of the additive of interest to obtain a calibration curve for determining the concentration of the additive of interest. The analysis has to be done when the concentrations of other additives are known or determined first.

A QC electro-analytical technique is to obtain plating response measurement of an unknown plating bath as is and can be performed quite regularly to control the level of different additives in a plating bath/electrolyte.

Electro-Analytical Method

FIG. 1 is a flow chart illustrating an exemplary electro-analytical method 100 for analyzing the concentration of one or more organic components in plating baths containing multiple-component organic additives using an organic chemical analyzer. Applicable organic analyzers include, but are not limited to, cyclic voltammetric strippers, cyclic pulsed voltammetric strippers, and pulsed cyclic galvano-static analyzers.

The method 100 in FIG. 1 includes preparing a supporting-electrolyte solution at step 110, preparing a testing solution at step 120, measuring an electrochemical response of the supporting-electrolyte solution and the testing solution using the organic chemical analyzer at step 130, and implementing an electro-analytical technique to determine the concentration of the organic additive in the plating bath from the electrochemical response measurements at step 140. The method is independently performed in real time for analyzing one organic additive component without the knowledge of the concentrations of other organic additives in a plating bath containing multi-component organic additives.

When determining the accelerator concentration using method 100, the testing solution may include the supporting-electrolyte solution and a production solution. The production solution may include a portion of the plating bath to be tested diluted with the supporting-electrolyte solution into a dilution factor or dilution ratio. The testing solution may further include one or more volumes of a standard solution having known concentration of one or more organic additives for the plating bath to be tested. Preferably, the one or more volumes of the standard solution are successively added to the testing solution in order to make up a series of testing solutions.

When determining the suppressor or leveler concentration using method 100, the testing solution may include the supporting-electrolyte solution and one or more volumes of a standard solution having known concentration of one or more organic additives for the plating bath to be tested. Preferably, the one or more volumes of the standard solution are successively added to the testing solution in order to make up a series of testing solutions.

Although the methods described herein employ the electro-chemical principle of CVS for copper plating as an example, the same approach may be used in any other electro-analytical electrochemical principles, such as CPVS and PCGA, that is based on the sensitivity of an electro-chemical response to trace amounts of organic additives in a plating bath. Embodiments of the invention may also be used to determine an unknown component in other plating baths with multi-component organic additives, such as nickel (Ni), cobalt (Co), and silver (Ag) plating, where the composition of a plating bath/solution is controlled by a control system, either manually or automatically, resulting in consistent metal deposition, and should not be limited to CVS techniques for copper plating.

Accelerators:

For analyzing the concentration of an accelerator in an unknown plating bath using an organic chemical analyzer and the method 100 as described herein, a MLAT technique utilizing the anti-suppression property of the accelerator is implemented. First of all, a supporting-electrolyte solution is prepared as described herein and an intercept plating response value is measured.

The intercept measurement is obtained without any added unknown plating bath and only the supporting-electrolyte solution is present in a cell/container of the organic chemical analyzer. Typically, for a MLAT technique to work properly using a CVS chemical analyzer for example, the intercept measurement, which is the anodic stripping area ($A_r$) of only the supporting-electrolyte solution and the first information/data point to be obtained, has to be constant regardless the changes in concentrations of other organic additives except the accelerator itself.

However, in the presence of other organic additives, such as a suppressor and a leveler, the leveler competes with both the accelerator and the suppressor for surface adsorption. Even if employing a VMS and a suppressor as the supporting-electrolyte solution, the intercept measurement can still be a function of the leveler concentrations.

Therefore, in one embodiment, the invention provides a method of analyzing an accelerator by including trace amounts of the accelerator into the supporting-electrolyte solution and compensating for the changes in intercept measurement of a MLAT technique as a function of the leveler concentrations. The intercept measurement can be kept constant if the supporting-electrolyte solution includes excess amounts of a suppressor and trace amounts of the accelerator in addition to a VMS solution, while the concentrations of organic additives other than the accelerator of interest, such as a suppressor and leveler in any unknown plating bath, may vary. As a result, accurate and reliable analysis of an accelerator is independently achieved by the method described herein, even in the presence of other organic additives and without knowing the concentrations of other organic additives, such as the suppressor and leveler in any unknown plating bath.

Suppressors:

For analyzing the concentration of a suppressor in an unknown plating bath using an organic chemical analyzer and the method 100 as described herein, a DT technique utilizing the suppression property of the suppressor is implemented. A dilution series of an unknown plating bath (diluted with a supporting-electrolyte solution) and a series of testing solutions having standard bath solutions at known concentrations (diluted with the supporting-electrolyte solution) are prepared. Using a CVS chemical analyzer for example, the dependence of the anodic stripping area on the suppressor concentration is then used to analyze the suppressor concentration in the unknown solution. However, the analysis accuracy and precision suffer if the other organic additives, such as an accelerator and a leveler in the unknown solution, exert significant interference to the dependence of the anodic stripping area on the suppressor concentration.

Therefore, in one embodiment, the invention provides a method of analyzing a suppressor to include trace amounts of the suppressor in an inorganic VMS solution to make up the supporting-electrolyte solution. As a result, the concentration ratio of the suppressor to an accelerator and of the suppressor to a leveler in the electrolyte cell/container tested by an organic chemical analyzer is greatly increased. In addition, the interference effect of other organic additives, such as the accelerator and leveler to the suppressor is greatly reduced and the accuracy and precision of the suppressor analysis are greatly improved.

Levelers:

For analyzing the concentration of a leveler in an unknown plating bath using an organic chemical analyzer and the method 100 as described herein, a DT technique utilizing the suppression property of the leveler is implemented.

The invention, in one embodiment, provides a method of analyzing a leveler by including excess amounts of other organic additives, such as a suppressor and an accelerator, in an inorganic VMS solution to make up the supporting-electrolyte solution. As a result, the interference effect of other organic additives, such as the accelerator and suppressor, to the leveler is greatly reduced and the accuracy and precision of the leveler analysis are greatly improved.

Electro-Chemical Deposition System:

Embodiments of the invention provide electro-analytical methods that can be performed in various electrochemical deposition systems. An electro-chemical deposition system generally includes a mainframe having a mainframe wafer transfer robot, a loading station disposed in connection with the mainframe, one or more processing cells disposed in connection with the mainframe, and an electrolyte supply fluidly connected to the one or more electrical processing cells. Generally, the electro-chemical deposition system includes a system controller for controlling an electrochemical deposition process and related components, a spin-rinse-dry (SRD) station disposed between the loading station and the mainframe, and an electrolyte replenishing system including an integrated chemical analyzer.

One example of an electrochemical deposition system that may be used herein is an Electra integrated Electro-Chemical Plating (iECP) System available from Applied Materials, Inc., of Santa Clara, Calif. In addition, any system enabling electrochemical deposition using the methods or techniques described herein may also be used.

Figure 2:
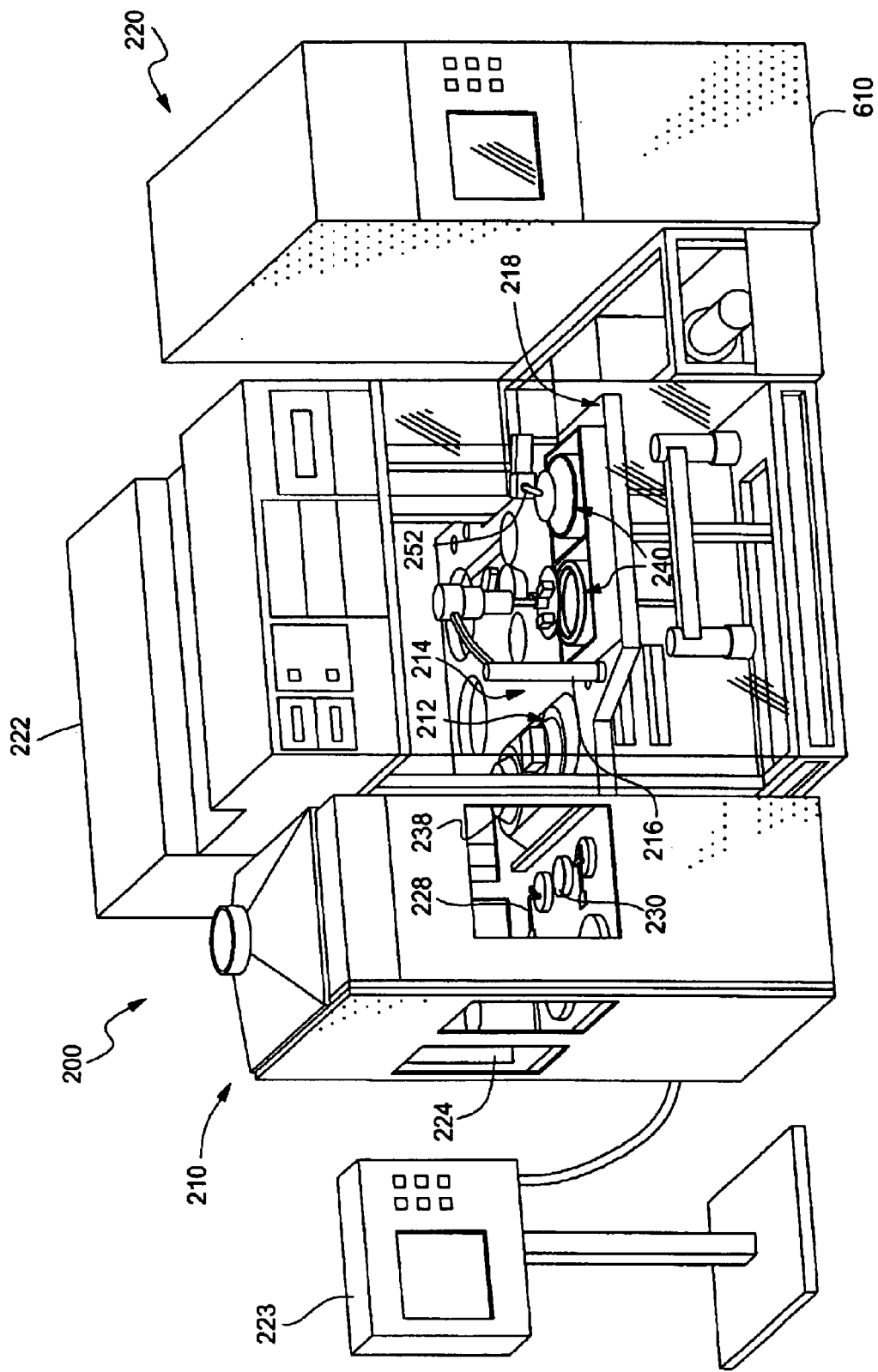
FIG. 2 is a perspective view of an electroplating system platform useful to perform methods described herein.

FIG. 2 is a perspective view of an electroplating system platform 200 of the invention. The electroplating system platform 200 generally includes a loading station 210, a spin-rinse-dry (SRD) station 212, a mainframe 214, and an electrolyte replenishing system 220. Additionally, the electroplating system platform 200 is enclosed in a clean environment using panels such as plexiglass panels.

The mainframe 214 generally includes a mainframe transfer station 216 and a plurality of processing stations 218. Each processing station 218 includes one or more processing cells 240. An electrolyte replenishing system 220 is positioned adjacent the electroplating system platform 200 and connected to the process cells 240 individually to circulate electrolyte used for the electroplating process. The electroplating system platform 200 also includes a control system 222, typically a programmable microprocessor. The control system 222 also provides electrical power to the components of the system and includes a control panel 223 that allows an operator to monitor and operate the electroplating system platform 200.

The loading station 210 typically includes one or more wafer cassette receiving areas 224, one or more loading station transfer robots 228 and at least one wafer orientor 230. The number of wafer cassette receiving areas, loading station transfer robots 228, and wafer orientor 230 included in the loading station 210 can be configured according to the desired throughput of the system. A wafer cassette containing wafers is loaded onto the wafer cassette receiving area 224 to introduce wafers into the electroplating system platform. The loading station transfer robot 228 transfers wafers between the wafer cassette and the wafer orientor 230. The wafer orientor 230 positions each wafer in a desired orientation to ensure that each wafer is properly processed. The loading station transfer robot 228 also transfers wafers between the loading station 210 and the SRD station 212.

Figure 3:
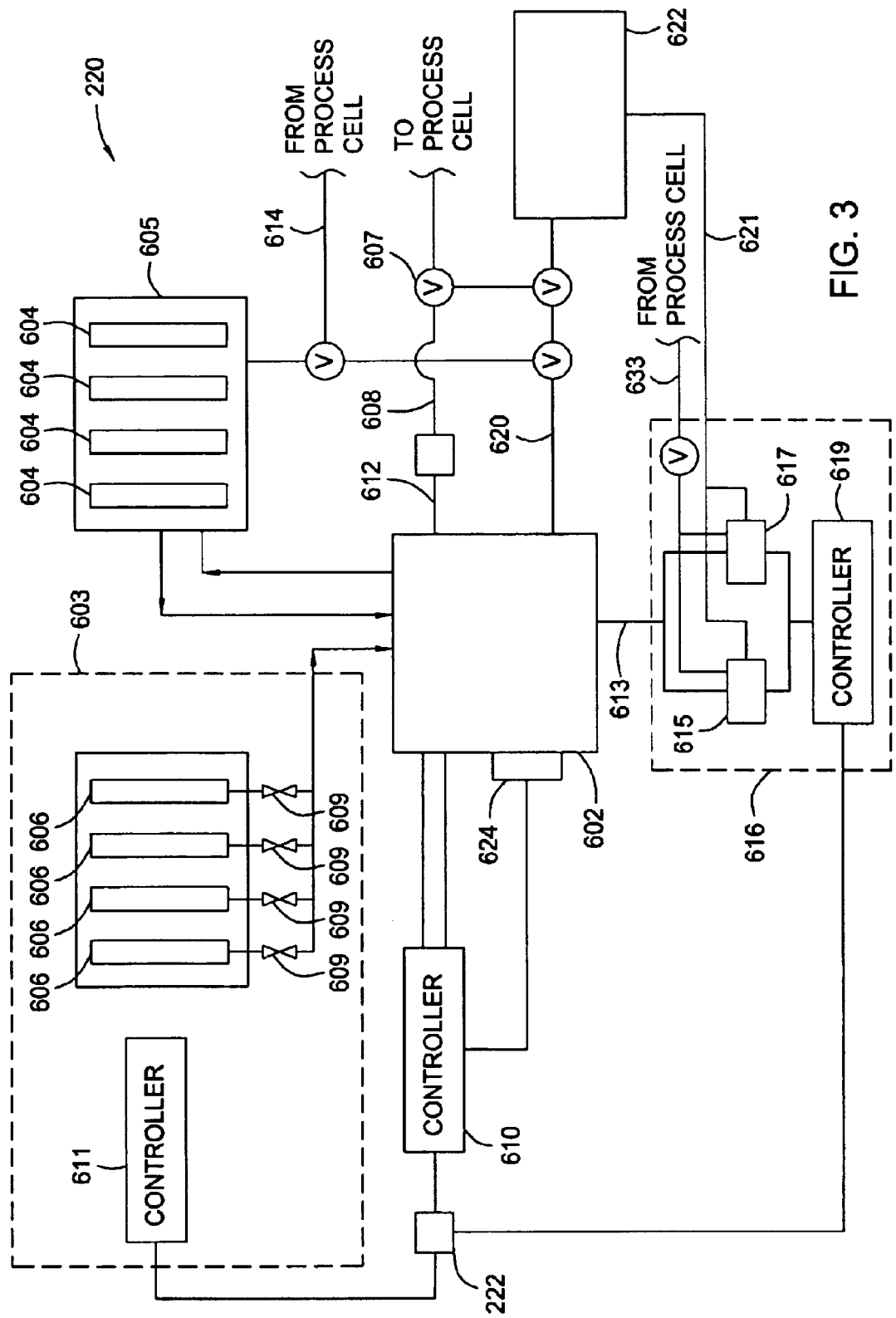
FIG. 3 is a schematic diagram of one embodiment of an electrolyte replenishing system 220.

FIG. 3 is a flow chart illustrating the electrolyte replenishing system 220, which includes a main controller 610, a main electrolyte tank 602, a dosing module 603, a filtration module 605, a chemical analyzer module 616, and an electrolyte waste disposal system 622 connected to the analyzing module 616 by an electrolyte waste drain 620. The electrolyte replenishing system 220 provides the electrolyte to the electroplating process cells 240 for the electroplating process. One or more controllers, such as controller 610, 611, and 619, control the composition of the electrolytes in the main tank 602 and the operation of the electrolyte replenishing system 220.

The controllers 610, 611, and 619 are usually independently operable but are typically integrated with the control system 222 of the electroplating system platform 200 to provide real-time analyses of the electroplating process and control of the chemical analyzer module 616, the dosing module 603, and other components. Alternatively, the chemical analyzer module 616 and the dosing module 603 may be integrated into one single module and may be controlled by one or more controllers to monitor and replenish the electrolyte from the electroplating process cells 240.

The main electrolyte tank 602 provides a reservoir for electrolyte and is connected to each of the electroplating process cells 240 through one or more fluid pumps 608, an electrolyte supply line 612, and valves 607. A heat exchanger 624 or a heater/chiller, which is disposed in thermal connection with the main tank 602 and operated by the controller 610, controls the temperature of the electrolyte stored in the main tank 602.

The dosing module 603 is connected to the main tank 602 by a supply line and includes a plurality of source tanks 606, or feed bottles, a plurality of valves 609, and a controller 611. The source tanks 606 contain the inorganic chemicals needed for composing the electrolyte and typically include deionized water, copper sulfate ($CuSO_4$), sulfuric acid ($H_2SO_4$), hydrochloric acid (HCl), and other additives such as glycol. The valves 609 associated with each source tank 606 regulate the flow of inorganic chemicals to the main tank 602. Activation of the valves 609 is accomplished by the controller 611, which is preferably connected to the control system 222 to receive signals therefrom.

The electrolyte filtration module 605 includes a plurality of filter tanks 604. An electrolyte return line 614 is connected between each of the process cells 240 and one or more filter tanks 604. The filter tanks 604 continuously remove the undesired solids in the used electrolyte before returning the electrolyte to the main tank 602 for re-use and replenishing, and facilitate re-circulation and filtration of the electrolyte in the main tank 602 to help maintain a consistent level of purity and thorough mixing of the electrolyte in the main tank 602.

The chemical analyzer module 616 includes at least one, and typically two or more, analyzers 615, 617 operated by the controller 619 and integrated with the control system 222 of the electro-chemical deposition system 200. The analyzer module 616 is fluidly coupled to the main tank 602 by a sample line 613 to provide continuous flow of electrolyte, standard plating solutions, supporting electrolyte solution, etc. from the main electrolyte tank 602 to the chemical analyzers, such as analyzers 615, 617. The analyzer module 616 is also coupled to the waste disposal system 622 by an outlet line 621.

The analyzer module 616 is also coupled to the one or more process cells 240 by an inlet line 633 to provide real-time chemical analysis of the chemical composition of the electrolyte inside each process cell 240 by the chemical analyzers, such as analyzers 615, 617. The number of analyzers required for a particular processing tool depends on the composition of the electrolyte. A first analyzer may be an inorganic analyzer, for example, an auto-titration analyzer to determine the concentrations of inorganic substances in the electrolyte, and the second analyzer may be an organic analyzer, for example, a cyclic voltammetric stripper (CVS), to determine the concentrations of organic substances. After the concentrations of specific chemical components of the electrolyte are analyzed, the dosing module 603 is then activated to deliver the proper proportions of the chemicals to the main tank in response to the information obtained by the chemical analyzer module 616.

Most analyzers are commercially available from various suppliers. A suitable auto-titration analyzer is available from Applied Materials, Inc. of Santa Clara, Calif., such as the Bantam analyzer™, and a cyclic voltammetric stripper is available from ECI Technology, Inc. of East Rutherford, N.J., such as the Quali-line™ QLCA analyzer. The auto-titration analyzer determines the concentrations of inorganic substances such as copper, chloride, and acid. The cyclic voltametric stripper determines the concentrations of organic substances such as various additives used as electrolytes in a plating bath.

The analyzers 615, 617 typically include standards and calibration schemes that enable the controller 619 to compensate for the drifts in measurements as the electrodes or sensors in the analyzers 615, 617 become corroded due to repeated use. The standards and calibration schemes are grouped according to the substances being analyzed by the analyzer. For example, an auto-titration analyzer includes standards and calibration schemes for the inorganic substances, and a CVS analyzer includes standards and calibration schemes for the organic substances. For example, Table 1 provides three standards for an analysis of copper and chloride contents in a plating bath at a process window between the low and high standards. By interpolating the relationship between the known contents in the standards and the measurements of an analyzer, and using various electro-analytical techniques, the analyzer becomes calibrated to provide accurate analysis of the substances in a testing plating bath.

TABLE 1

Standards for copper and chloride contents

|  | Copper | Chloride |
| --- | --- | --- |
| Standard 1 (low) | 40 g/l | 40 ppm |
| Standard 2 (medium) | 50 g/l | 70 ppm |
| Standard 3 (high) | 60 g/l | 100 ppm |

In one embodiment of the invention, the method 100 of FIG. 1 as provided herein is integrated with the controller 619 for the chemical analyzer module 616 and the control system 222 for the electrochemical deposition system 200.

In operation, a sample of supporting-electrolyte solution prepared according to embodiments of the invention, such as the step 110 of FIG. 1, is flowed to the analyzer module 616 from the main electrolyte tank 602 via the sample line 613. A portion of the sample is delivered to the auto-titration analyzer 615 and a portion is delivered to the CVS 617 for the appropriate analysis. The controller 619 initiates command signals to operate the analyzers 615 and 617 in order to generate data and electrochemical responses of the supporting-electrolyte solution are measured by the analyzers 615, 617. The controller 619 also initiates the next step, such as the step 120 of FIG. 1, for the flowing of an unknown sample of electrolyte or a portion of the unknown testing sample from the process cell 240 to the analyzer module 616 via the inlet line 633, with or without diluting with the supporting-electrolyte solution from the main electrolyte tank 602 via the sample line 613.

To analyze additive concentrations in electroplating solutions, plating responses are measured for various concentrations of production baths/solutions, supporting-electrolyte solution, testing solutions, standard solutions, calibration solutions, and/or in the presence or absence of additives, depending upon which analytical method and which type of additive needed to be tested. The calculations required to obtain the active concentrations from the results of these measurements are already programmed into the controller 619 and the control system 222 for various analyzer modules and ECP systems.

By implementing the method 100 of FIG. 1 and the necessary electro-analytical techniques programmed in the controller 619, electrochemical response measurements of the various testing solutions, production solutions, etc., as described in FIG. 1 are obtained and the concentration of the organic additive of interest is determined. For example, when analyzing the concentration of an accelerator in an unknown plating bath using the method 100 as described herein, a plating response value of a supporting-electrolyte solution made up of VMS solution, up to about 5 ml/L of the accelerator, brightener, or anti-suppressor, and between about 10 ml/L and about 60 ml/L of a suppressing agent is measured first. Then, the a testing solution containing a portion of the unknown sample of electrolyte from the process cell 240 is flowed into the organic analyzer to mix with the supporting-electrolyte solution for the accelerator (the resulting mixture is also referred to as a production solution) and another plating response value is obtained from the measurement of the organic analyzer. Optionally, one or more volumes of standard solution with known concentrations of organic additive of interest are then flowed into the organic analyzer to mix with the testing solution or the production solution for additional one or more plating response measurements. Finally, the controller 619 implements a specified electro-analytical technique for the accelerator, such as a MLAT technique to determine on-line analysis of the concentration of the accelerator in the unknown plating bath from the process cell 240.

Although the sample may be taken periodically, preferably a continuous flow of electrolyte is maintained to the analyzer module 616. The information from the chemical analyzers 615 and 617 is then communicated to the control system 222. The control system 222 processes the information and transmits signals, which include user-defined chemical dosage parameters, to the dosing controller 611. The received information is used to provide real-time adjustments to the source chemical replenishment rates by operating one or more of the valves 609, thereby maintaining a desired, and preferably constant, chemical composition of the electrolyte throughout the electroplating process. The waste electrolyte from the analyzer module is then flowed to the waste disposal system 622 via the outlet line 621.

The methods described herein provide accurate real-time, on-line analysis of the electrolyte and facilitate a closed-loop analysis that can be performed with an organic analyzer attached to the system. Such integration extends the useful life of the electrodes or sensors and decreases the frequency of system interruptions due to replacement of these components.

The analyzer module 616 shown in FIG. 3 is merely illustrative. In another embodiment, each analyzer may be coupled to the main electrolyte tank by a separate supply line and be operated by separate controllers. Persons skilled in the art will recognize other embodiments. Various alternatives may be employed for real-time monitoring and adjustments of the plating additives. For example, control of the dosing module 603 may be manually adjusted by an operator observing the output values provided by the chemical analyzer module 616. The system software may allow for both an automatic real-time adjustment mode as well as an operator (manual) mode. Further, a single controller or multiple controllers may be used to operate various components of the system such as the chemical analyzer module 616, the dosing module 603, and the heat exchanger 624.

The electrolyte replenishing system 220 further includes an electrolyte waste drain 620 connected to an electrolyte waste disposal system 622 for safe disposal of used electrolytes, chemicals and other fluids used in the electroplating system, and may include a number of other components. For example, one or more additional tanks for storage of chemicals for a wafer cleaning system, such as the SRD station, and double-contained piping for hazardous material connections may be employed to provide safe storage and transport of the chemicals throughout the system. Optionally, the electrolyte replenishing system 220 includes connections to additional or external electrolyte processing system to provide additional electrolyte supplies to the electroplating system 200.

EXAMPLES

Examples of electro-analytical methods for determining the concentration of an organic additive or electrolyte of interest in an acidic or basic metal plating bath are presented herein. The ECP system used herein is an Electra iECP system available from Applied Materials, Inc. of Santa Clara, Calif. and a CVS organic analyzer is used under CVS conditions of an electrode rotational speed of between about 100 rpm to about 2500 rpm, an electric potential rate of between about 50 mV/s to about 500 mV/s and a negative potential limit as of between about −0.1 V and about −0.5 V, with respect to a silver/silver chloride (Ag/AgCl) type reference electrode.

Typical concentrations of the components of a plating bath that may be used in such Electra iECP system are as follows. The concentrations of the inorganic components may be, for example, between about 5 grams per liter (g/L) to about 80 g/L of copper sulfate, such as between about 10 g/L and about 60 g/L, between about 30 ppm and about 200 ppm of hydrochloric acid, and between about 5 g/L to about 200 g/L of sulfuric acid. The concentrations of the organic components in a plating bath that can be analyzed by the methods described herein may be, for example, between about 0.01 ml/L to about 25 ml/L of an accelerator, brightener, or anti-suppressor, between about 0.01 ml/L and about 60 ml/L of a suppressor, carrier, surfactant, or wetting agent, and between about 0.01 ml/L to about 20 ml/L of a leveler, over-plate inhibitor, or grain refiner. Various organic components used herein were purchased from Shipley Inc. of Marborough, Massessa, or Enthone OMI of New Haven, Conn.

Figure 4A:
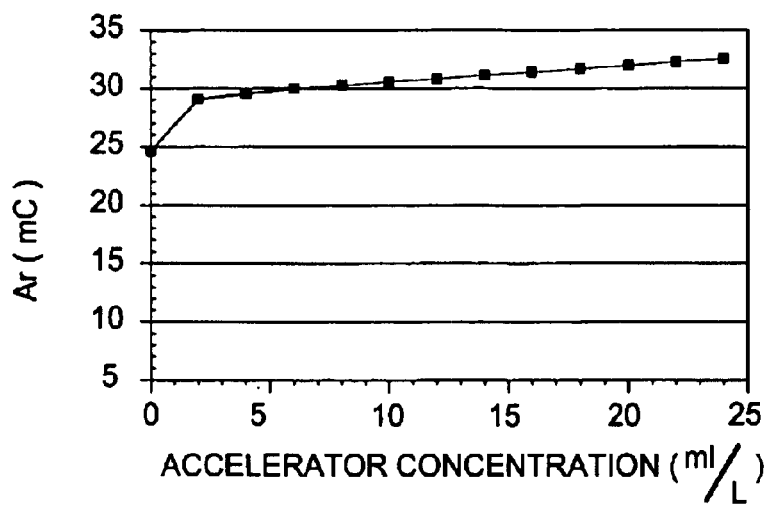
FIGS. 4A–4C illustrate CVS responses for three types of organic additives, an accelerator, a suppressor, and a leveler, respectively.
Figure 4B:
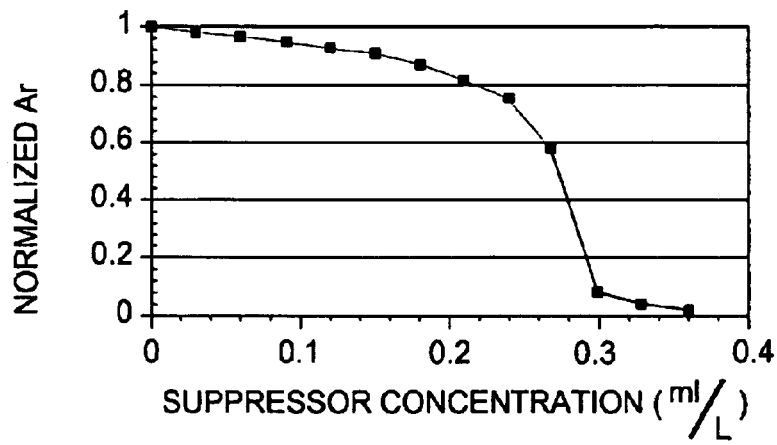
Figure 4C:
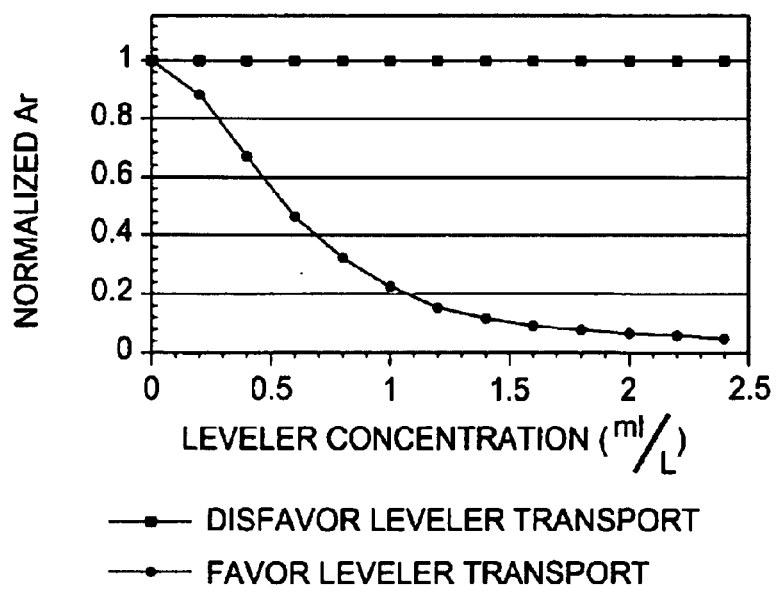

Measurements of typical CVS plating-response for three types of organic additives are tested and demonstrated in FIGS. 4A–4C for an accelerator, a suppressor, and a leveler, respectively, in the presence of a VMS solution. The stripping area ($A_r$) of anodic stripping charges are usually plotted as integrated anodic currents in millicoulombs (mC) for anodic copper stripping, correlate directly with the amount of cathodic copper deposited (copper deposition rate), and are thus measured as a function of the concentration of an added additive, such as an accelerator, a suppressor, and a leveler. Each type of organic additive that needed to be measured is added to a process cell of a CVS analyzer, containing VMS solution inside the process cell.

FIG. 4A demonstrates the results of CVS responses for an accelerator. The accelerator enhances plating-response measurements without saturation until at very high concentrations of about 24 ml/L or higher.

In FIG. 4B, normalized $A_r$ values ($A_r$ values compared to no additive addition) are plotted against a series of suppressor concentrations showing the suppressor as the most sensitive component for CVS analysis. The suppressor inhibits/suppresses metal deposition on an inert electrode inside the process cell of the CVS analyzer as measured by anodic stripping charges. Saturation of the suppression is reached at a concentration as low as about 0.3 ml/L, where the stripping charges are so low that there is little or no metal deposition.

FIG. 4C demonstrates the results of CVS responses for a leveler. The top line with square dots is the CVS response measurements under CVS cycling conditions disfavoring leveler transport and the bottom line with diamond dots is the CVS response measurements under CVS conditions favoring leveler transport. Under optimum conditions favoring leveler transport, the leveler inhibits copper over-plating and saturation of the inhibition is reached at a concentration of at least about 1.5 ml/L. CVS responses for the leveler are very sensitive to CVS conditions and the leveler may be ineffective for inhibiting copper deposition under conditions disfavoring leveler transport, thus there is no leveler present on the surface of an inert electrode to be plated inside a CVS analyzer.

In conclusion, FIGS. 4A–4C demonstrate that in the presence of all three organic components in a plating bath, the only component that can be directly analyzed without great interference from the other two components is the suppressor because the sensitivity of CVS responses for the suppressor is the highest among all three organic additives such that saturation of the enhancement or inhibition is reached at a low concentration, but that is not the case for the accelerator and the leveler.

Example A

Determination of the Concentration of an Accelerator in a Plating Bath:

The conclusion from FIGS. 4A–4C has to be taken into account for analyzing the concentration of an accelerator in an unknown plating bath. For analyzing an accelerator, a brightener, or an anti-suppressor, the linear dependence of anodic stripping area on the accelerator concentration is employed in a method such as the electro-analytical method 100 of FIG. 1 using a CVS organic analyzer.

Typically, the concentration of a suppressor in the plating bath is higher than, or at least comparable to, the concentration of an accelerator. The results shown in FIGS. 4A–4C suggest that analyzing the concentration of an accelerator has to be done in the presence of a suppressor, such as excess amounts of a suppressor.

Figure 5:
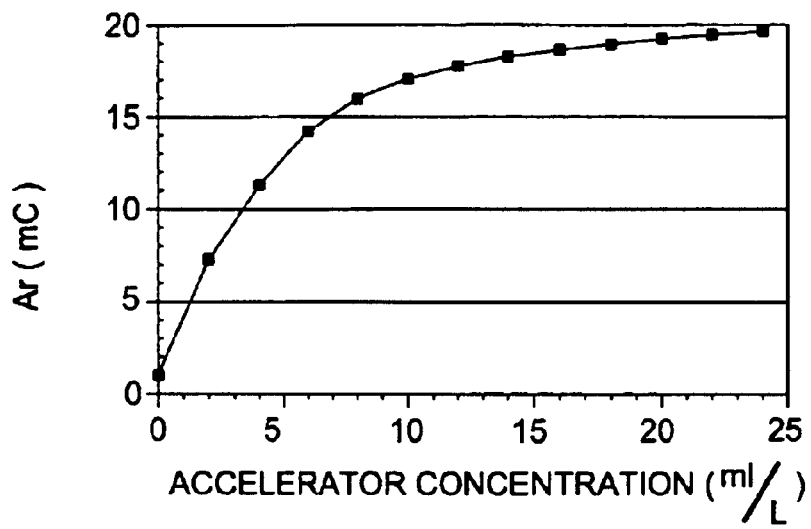
FIG. 5 illustrates CVS responses for the analysis of an accelerator in a supporting-electrolyte solution composed of inorganic Virgin Make-up Solution (VMS) and excess amounts of a suppressor.

Therefore, FIG. 5 illustrates anodic stripping area measurements using a supporting-electrolyte solution, which includes excess amounts of a suppressor, such as about 10 ml/L or more, in addition to VMS. The results in FIG. 5 demonstrate that an accelerator can act as an anti-suppressor in the presence of excess amounts of a suppressor, such as about 15 ml/L of the suppressor as used in FIG. 5, and anodic stripping area measurements inside the CVS analyzer are lower under the same accelerator concentrations as compared to the accelerator analysis of FIG. 4A.

However, including excess amounts of a suppressor in the supporting-electrolyte solution to reduce the interference effect from the suppressor present in the unknown solution is not sufficient for analyzing the concentration of an accelerator. Other organic additives, such as a leveler, over-plate inhibitor, or grain refiner, will also interfere with the linear dependency of anodic stripping area for accelerator analysis, including the slope and intercept values of a MLAT technique. Such interference effect from a leveler is further explored in FIG. 6.

Figure 6:
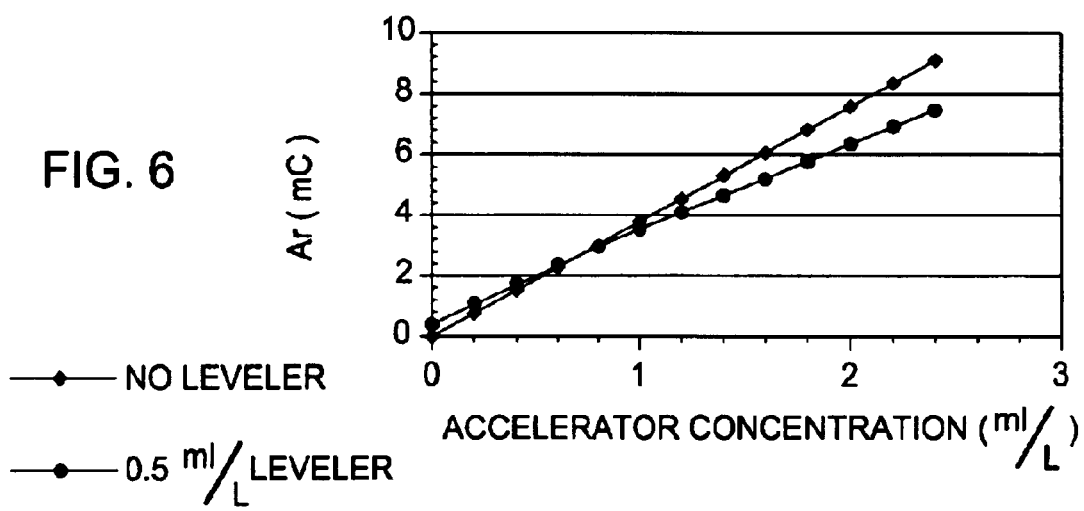
FIG. 6 illustrates CVS responses for the analysis of an accelerator in a supporting-electrolyte solution composed of inorganic VMS and excess amounts of a suppressor.

FIG. 6 illustrates CVS response curves versus a series of accelerator concentrations in a supporting-electrolyte solution that includes inorganic VMS and excess suppressor concentration of about 50 ml/L and demonstrates linear dependency under accelerator concentrations such as about 2.5 ml/L or less. The linear response curve with circle dots shows CVS responses performed with the addition of a leveler at a concentration of about 0.5 ml/L to the supporting-electrolyte solution as compared to the response curve with diamond dots performed without leveler addition.

The two response curves of FIG. 6 suggest an interference effect from a leveler when analyzing the concentration of an accelerator. Under the specific CVS condition performed, the leveler inhibits CVS responses at higher accelerator concentration, such as about 0.9 ml/L or higher, but enhances CVS responses in the presence of trace amounts of the accelerator, such as about 0.7 ml/L or less, so that the intercept (b) value in the linear response curve (y=ax+b) using a MALT analysis to analyze accelerator concentration is dependent on the leveler concentration.

Figure 7:
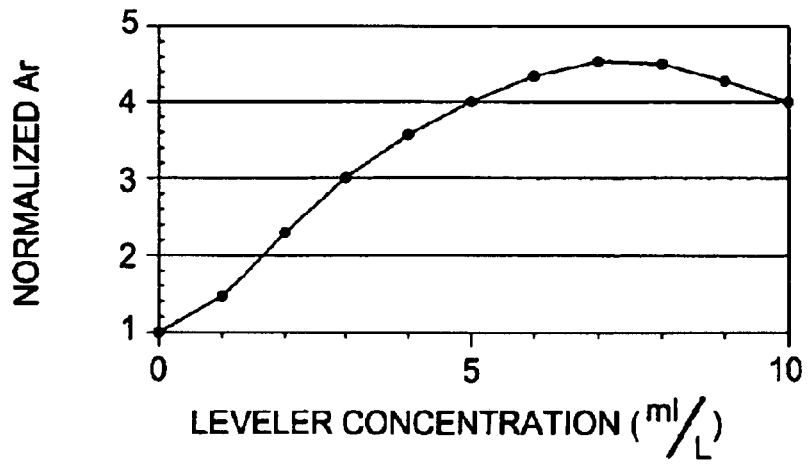
FIG. 7 illustrates the interference effect of a leveler in a supporting-electrolyte solution composed of inorganic VMS and excess amounts of a suppressor.

One hypothesis for such enhancement or interference effect at low accelerator concentration from the leveler is that, in the presence of excess suppressor and trace amounts of the accelerator, the leveler adsorbs on the electrodes and competes with the suppressor so that the leveler acts as an additional anti-suppressor in the supporting-electrolyte solution and thus enhances metal deposition, contrary to its normal function of inhibiting metal over-plating, which is demonstrated in FIG. 7 below to show the leveler as an anti-suppressor in the presence of excess amount of suppressors.

In addition, FIG. 6 also suggests that the presence of the leveler in the testing solutions not only affects the absolute $A_r$ response values, the Y-axis intercepts, but also the slopes of the two $A_r$ response lines under different accelerator concentrations. Therefore, the Y-axis intercept values and slope changes in FIG. 6 are a function of the leveler concentrations present in the testing solutions.

However, when analyzing accelerator concentration in an unknown plating bath, the implementation of a MLAT technique makes the slope of $A_r$ responses to accelerator concentrations a non-relevant factor for accelerator analysis, because using the MLAT technique, $A_r$ responses are highly sensitive to typical accelerator concentrations used in the plating bath such that the slope is large enough to perform a linear regression of the slope values by MLAT. Although the slope does not need correction, only intercept dependence on leveler concentration must be corrected in order to accurately analyze accelerator concentrations.

In FIG. 6, the two response curves cross at about 0.8 ml/L of the accelerator concentration, which is independent of leveler concentrations in the original solution for CVS testing under the CVS condition performed, even though the slopes of the two curves has changed. Therefore, by providing about 0.8 ml/L of the accelerator in the supporting-electrolyte solution, the intercept value will be the plating response measurement in the presence of the supporting electrolyte solution having about 0.8 ml/L of the accelerator, and will then be independent of the leveler concentration inside plating cell as long as leveler concentration is within a specific concentration range good for filling microfeatures, such as between about 0.01 ml/L to about 20 ml/L.

The results in FIG. 6 support the method of analyzing the concentration of an accelerator, brightener, or anti-suppressor, by implementing a MLAT technique together with an organic chemical analyzer to include trace amounts of the accelerator, such as up to about 5 ml/L, in addition to inorganic VMS and excess concentration of a suppressor, such as between about 10 ml/L and about 60 ml/L, in a supporting-electrolyte solution, such that interference effects from other organic additives, such as a leveler and the suppressor to the accelerator, is at its minimal level.

The trace amounts of the accelerator needed to render an interference effect from the leveler may vary according to the range of concentrations of the leveler and suppressor added, the chemical natures of various organic additives, and the CVS conditions, such as the electrode rotational speed, electric potential rate, and a negative potential limit.

Under the CVS conditions of FIG. 6, the supporting-electrolyte solution for analyzing the accelerator using the method 100 of FIG. 1 includes inorganic VMS, excess suppresser concentrations at about 20 ml/L, and trace amounts of the accelerator at about 0.8 ml/L. As a result, when such a supporting-electrolyte solution is prepared for analyzing accelerator concentration in an unknown plating bath using the method 100 of FIG. 1, the thus measured intercept plating response value is independent of the concentrations of both the suppressor and the leveler.

FIG. 7 illustrates $A_r$ values of CVS responses measured at various leveler concentrations under the same CVS conditions as for FIG. 6 and in a supporting-electrolyte solution containing inorganic VMS and about 50 ml/L of excess suppressor. The leveler concentration of about 0.5 ml/L in FIG. 6 is quite low for a normal plating bath. Therefore, a range of leveler concentrations is investigated in FIG. 7. The results are normalized to $A_r$ value with no leveler addition ($A_r$ value with leveler addition divided by $A_r$ values with no leveler addition). As a result, the Y-axis values in FIG. 7 represent the changes of the Y-axis intercept values as they would be in FIG. 6 under the same CVS conditions.

The results of FIG. 7 support the conclusion that a leveler acts as an anti-suppressor when placed together with a suppressor to enhance the plating CVS response such that by varying the leveler concentration, different interference effect is observed, as compared to no leveler addition. The more leveler added in the solution, the higher the intercept values and hence the higher the interference effect for analyzing accelerator concentration will be. The amount of the accelerator that is necessary to be added to the supporting-electrolyte solution to be employed in the method 100 of FIG. 1 for analyzing accelerator concentration can then be determined for different plating baths or at different time points during metal plating having different range of leveler concentration.

Example B

Determination of the Concentration of a Suppressor in a Plating Bath:

For analyzing the concentration of a suppressor, a method based on a DT technique such as the electro-analytical method 100 of FIG. 1 is used together with an organic chemical analyzer, such as a CVS organic analyzer. The unknown suppressor concentration with minimal interference effect either from an accelerator or a leveler can be determined by including trace amounts of the suppressor, such as up to about 0.5 ml/L, into a supporting-electrolyte solution.

Figure 8:
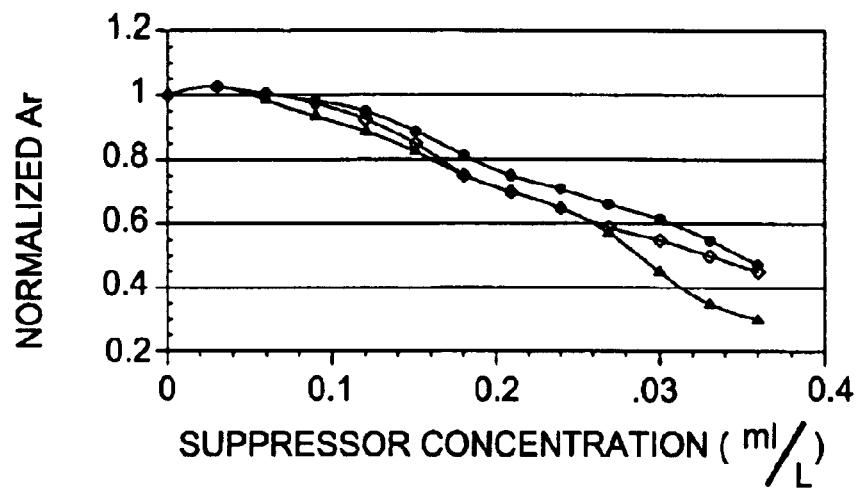
FIG. 8 illustrates the analysis of a suppressor using dilution titration (DT) technique in a supporting-electrolyte solution composed of only inorganic VMS.

FIG. 8 illustrates the analysis of three different plating solutions containing different organic additives components. Calibration solutions for all three plating solutions are prepared by diluting with a supporting-electrolyte solution composed of only inorganic VMS, in this case. The corresponding $A_r$ values are measured to demonstrate the dependence of $A_r$ values on different suppressor concentration present in various plating solutions inside a CVS cell/container. Only the normalized CVS $A_r$ values (CVS measurements of the plating solutions divided by the measurement of only the supporting-electrolyte solution) are plotted in FIG. 8.

The effective suppressor concentrations present in the dilution series of an unknown plating bath of interest need to be diluted to a low level to provide CVS measurements, such as about 0.4 ml/L or less under the CVS conditions for FIG. 8. This is because the sensitivity of CVS responses for suppressor is the highest among all three organic additives and saturation of the suppression is reached as low as about 0.4 ml/L.

In FIG. 8, the response curve with solid circle dots represents a plating solution having a suppressor concentration of about 5 ml/L. The response curve with blank diamond dots represents a plating solution having an accelerator concentration of about 6 ml/L and a suppressor concentration of about 5 ml/L. The response curve with solid triangle dots is for plating solution having a leveler concentration of about 5 ml/L in addition to a suppressor concentration of about 5 ml/L.

Even though the suppressor present in these three plating solutions in FIG. 8 is at the same concentration of about 5 ml/L, the response curves for the three plating solutions do not overlap with each other. The results in FIG. 8 indicate that, because of such discrepancy for the three response curves, suppressor measurement is going to be a problem in the presence of an accelerator and/or leveler. The problem is overcome by adding trace amounts of the suppressor into the supporting-electrolyte solution to increase the sensitivity of the CVS measurements toward the suppressor and is investigated in FIG. 9.

Figure 9:
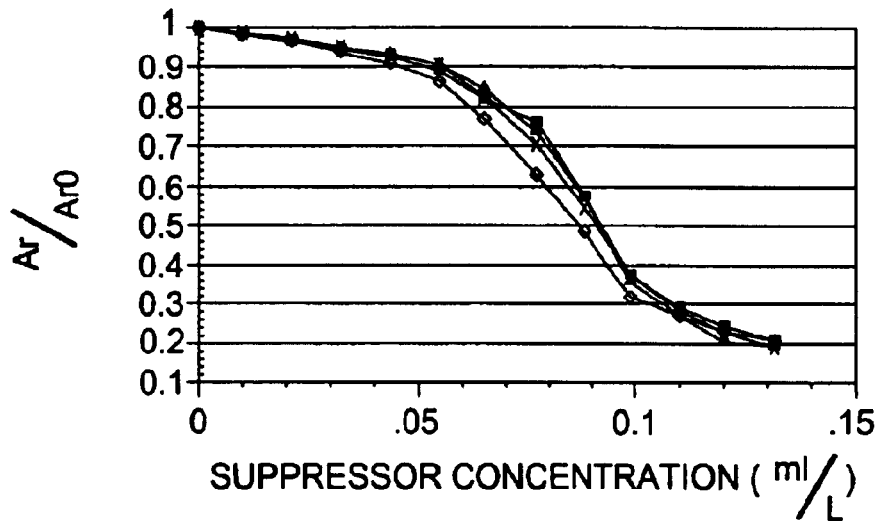
FIG. 9 illustrates the analysis of a suppressor using DT technique in a supporting-electrolyte solution composed of inorganic VMS and about 0.2 ml/l of the suppressor.

FIG. 9 illustrates the analysis of suppressor concentrations in a modified supporting-electrolyte solution composed of inorganic VMS and trace amounts of a suppressor at about 0.2 ml/L. Due to the high sensitivity of the CVS response for the suppressor, for example, under the CVS conditions of FIG. 4B, CVS response is already saturated at about 0.3 ml/L of suppressor concentration, therefore, the range of the suppressor concentration that can be added to the supporting-electrolyte solution is between about zero and about 0.3 ml/L.

In FIG. 9, CVS measurements for three plating solutions which are the same plating solutions as in FIG. 8, are compared, however about 0.2 ml/L of the suppressor is included in the modified supporting-electrolyte solution in addition to the inorganic VMS solution. The response curves are plotted against the suppressor concentration present in a different set of dilution series of the plating solutions, prepared by on-line real time dilution with the modified supporting-electrolyte solution. The three response curves in FIG. 9 are very similar and the results support a method of analyzing suppressor concentration in an unknown plating bath by comparing the slopes of different response curves at a chosen/predetermined endpoint using a DT electro-analytical technique. For example, the endpoint in a DT technique can be chosen at a normalized $A_r/A_{r0}$ value of about 0.5.

By adding about 0.2 ml/L of suppressor into the modified supporting-electrolyte solution, the initial concentration ratio for the organic additives present in the dilution series of the plating solutions for analysis is destroyed to reach a new equilibrium. Using the modified supporting-electrolyte solution, suppression of the CVS responses is saturated at a lower effective suppressor concentration of between about 0.12 ml/L and about 0.15 ml/L, as compared to and about 0.35 ml/L or higher in FIG. 8. Therefore, the addition of trace amounts of the suppressor into the modified supporting-electrolyte solution helps remove or reduce the interference effect from an accelerator or a leveler to a suppressor. The results from FIGS. 8 and 9 support a method of reliably and accurately determining the concentration of a suppressor, carrier, surfactant, or wetting agent by a DT technique to include trace amount of the suppressor, carrier, surfactant, or wetting agent into a supporting-electrolyte solution.

Example C
Determination of the Concentration of a Leveler in a Plating Bath:

For analyzing the concentration of a leveler, a method based on a DT technique such as the electro-analytical method 100 of FIG. 1 is used together with an organic chemical analyzer, such as a CVS organic analyzer. The unknown leveler concentration with minimal interference effect either from an accelerator or a leveler can be determined by including excess amounts of other organic additives, such as up to about 60 ml/L of an accelerator and up to about 60 ml/L of a suppressor, into a supporting-electrolyte solution.

Figure 10:
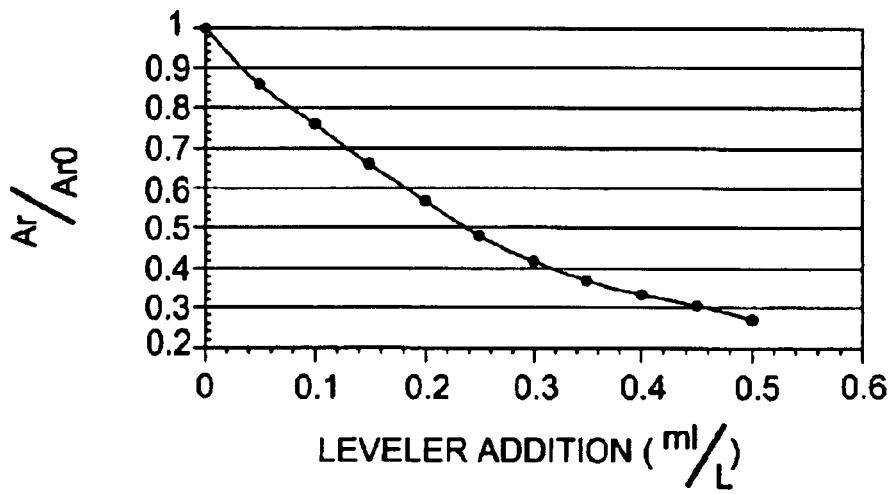
FIG. 10 illustrates the analysis of a leveler in the presence of excess amounts of an accelerator and a suppressor.

FIG. 10 illustrates the analysis of the concentration of a leveler in the presence of such supporting-electrolyte solution as an example to demonstrate how an additive can be independently analyzed without knowing the concentration of other additives in an unknown plating bath, contrary to most available on-line CVS tools. To analyze a third additive component (generally a leveler or a suppressor) in a metal plating bath containing three types of organic additives, most CVS analyzers require information regarding the concentration of the other two additives. This severely limits the user's ability to analyze the concentration of the third additive at any given time.

In FIG. 10, the leveler behaves as an effective suppressor in the supporting-electrolyte solution containing excess amounts of a suppressor and an accelerator in addition to inorganic VMS, at a concentration of about 30 ml/L of a suppressor and about 15 ml/L of an accelerator, such that the analysis is very sensitive to the concentrations of the leveler in a plating bath. The result supports the hypothesis that once there are enough suppressors and accelerators in the supporting-electrolyte solution for CVS measurements, a small variation of the actual concentrations of the accelerator and suppressor inside the testing plating bath does not matter anymore and does not interfere with the analysis of the leveler concentration.

The results shown in FIG. 10 support a method of reliably and accurately determining the concentration of a leveler by a DT technique to include excess amounts of all other organic additives except the leveler into a supporting-electrolyte solution. Typically, for an unknown plating bath, the concentration of the leveler, over-plate inhibitor, or grain refiner can be determined first using the method 100 of FIG. 1 described herein, followed by the methods described herein for determining the concentrations of other organic additives.

Figure 11A:
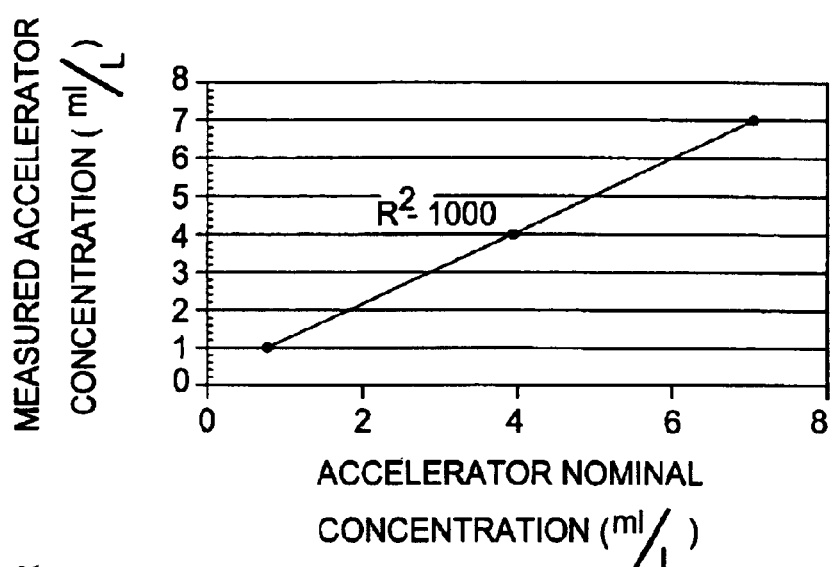
FIGS. 11A–11C illustrates performance analyses using methods described herein for a copper plating bath with three types of organic additives, an accelerator, a suppressor, and a leveler, respectively.
Figure 11B:
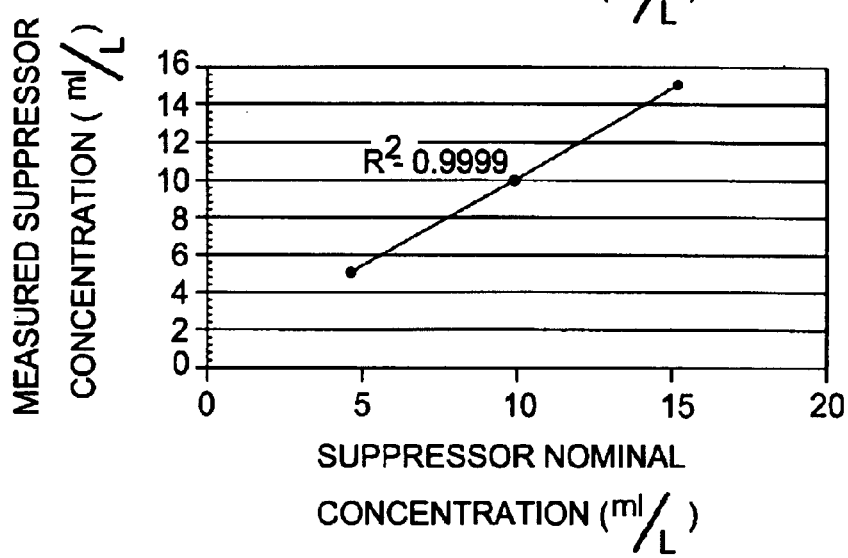
Figure 11C:
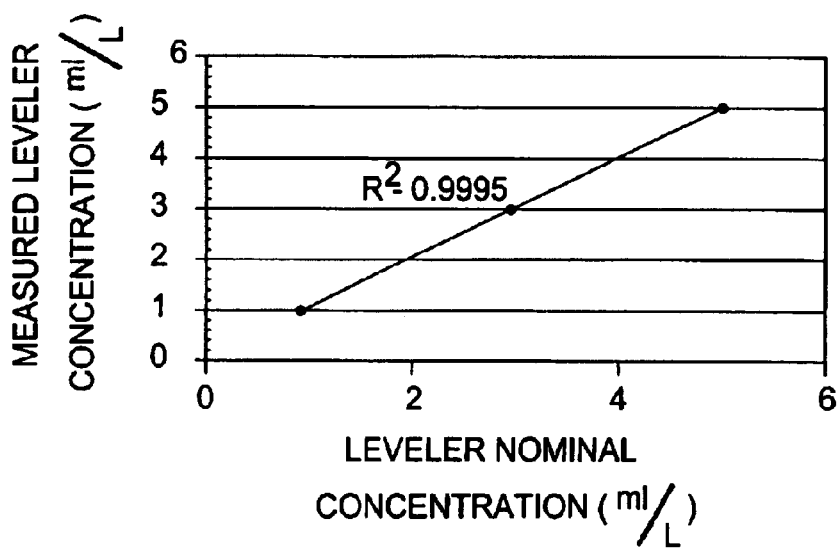

Finally, FIG. 11 illustrates the final performance analysis using methods described herein for copper plating using three types of organic additives. The plating solutions tested here are three fresh bath samples containing low, target, and high concentrations of all these respective organic additives. FIGS. 11A–11C show the measured additive concentrations against the nominal concentration for an accelerator, a suppressor, and a leveler, respectively. Nominal concentration means the known concentration prepared, and measured concentration is the deduced concentration for a particular plating bath using MLAT and DT techniques. In FIG. 11, the results show that the methods described and the supporting-electrolyte solutions prepared as described are very accurate for determining the concentration of the three kinds of organic components, showing extremely linear response with correlation R square values for all three additives at about 0.999 or higher.

The results in FIG. 11 also provide an appropriate process window for each of the three types of organic additives so that the electro-analytical methods described herein can be used to measure additive concentrations at a range between the tested low and high additive concentrations. The results also prove that good performance is observed for determining the concentrations of these three types of organic additives using the appropriate CVS cycling parameters and supporting-electrolyte solutions prepared as described.

While the foregoing is directed to various embodiments of the invention, other and further embodiments of the invention may be devised without departing from the basic scope thereof. The scope of the invention is determined by the claims that follow.

What is claimed is:

1. An electro-analytical method for determining the concentration of an organic additive of interest in a plating bath, having an unknown conformation including the organic additive and a suppressing agent to affect the quality of a metal to be plated, using an organic chemical analyzer operating on the basis of an electro-analytical principle, comprising:

preparing a supporting-electrolyte solution, comprising a virgin make up solution of all inorganic substances of the plating bath, trace amounts of the organic additive of interest, and excess amounts of the suppressing agent of the plating bath;

preparing a testing solution, comprising the supporting-electrolyte solution and a production solution, wherein the production solution comprises a portion of the plating bath;

measuring an electrochemical response of the supporting-electrolyte solution and the testing solution using the organic chemical analyzer; and determining the concentration of the organic additive of interest in the plating bath from the electrochemical response measurements.

2. The method of claim 1, wherein the concentration of an organic additive of interest selected from the group consisting of an accelerator, brightener, and anti-suppressor is determined independently of knowledge of the concentration of a suppressor, leveler, and other organic additives.

3. The method of claim 1, wherein the supporting-electrolyte solution comprises the virgin make up solution, trace amounts of the organic additive of interest selected from the group consisting of accelerator, brightener, and anti-suppressor, and excess amounts of the suppressing agent selected from the group consisting of suppressor, carrier, surfactant, and wetting agent.

4. The method of claim 1, wherein the amount of the organic additive of interest in the supporting-electrolyte solution is about 5 milliliters per liter (ml/L) or less.

5. The method of claim 1, wherein the amount of a suppressing agent of the plating bath in the supporting-electrolyte solution is between about 10 ml/L and about 60 ml/L.

6. The method of claim 1, wherein the testing solution further comprises one or more volumes of a standard solution, comprising known concentration of one or more organic additives for the plating bath.

7. The method of claim 1, wherein the concentration of the organic additive of interest in the plating bath is determined by implementing an electro-analytical technique selected from the group consisting of Modified Linear Approximation Technique (MLAT), Dilution Titration (DT), Response Curve (RC), and Quick Check (QC) techniques.

8. The method of claim 1, wherein the electrochemical response is selected from the group consisting of anodic stripping charge in milicoulombs, cathodic deposition charge in milicoulombs, anodic stripping rate, cathodic deposition rate, anodic stripping area, cathodic deposition area, electric current in milliampules, electrical potential in milivolts, differential electrical plating potential between cathodic and reference electrodes, AC current, DC current, and differential current.

9. The method of claim 1, wherein the electro-analytical principle is selected from the group consisting of Cyclic Voltammetric Stripping (CVS), Pulsed Cyclic Galvanostatic Analysis (PCGA), and Cyclic Pulsed Voltamic Stripping (CPVS).

10. The method of claim 1, wherein the method is applied to an acidic or basic metal plating bath and the metal to be plated is selected from the group consisting of copper, nickel, cobalt, silver, and combinations thereof.

11. An electro-analytical method for determining the concentration of an organic additive of interest, affecting the quality of a metal to be plated in a plating bath, using an organic chemical analyzer operating on the basis of an electro-analytical principle, comprising:

preparing a supporting-electrolyte solution, comprising a virgin make up solution of all inorganic substances of the plating bath and trace amounts of the organic additive of interest;

preparing a testing solution, comprising the supporting-electrolyte solution and one or more volumes of a standard solution, wherein the standard solution comprises known concentration of one or more organic additives for the plating bath;

measuring an electrochemical response of the supporting-electrolyte solution and the testing solution using the organic chemical analyzer; and determining the concentration of the organic additive of interest in the plating bath from the electrochemical response measurements.

12. The method of claim 11, wherein the concentration of an organic additive of interest selected from the group consisting of a suppressor, carrier, surfactant, and wetting agent is determined independently of knowledge of the concentrations of an accelerators, leveler, and other organic additive in the plating bath.

13. The method of claim 11, wherein the supporting-electrolyte solution comprises the virgin make up solution and trace amounts of the organic additive of interest selected from the group consisting of suppressor, carrier, surfactant, and wetting agent.

14. The method of claim 13, wherein the amount of the organic additive of interest in the supporting-electrolyte solution is about 0.5 milliliters per liter (ml/L) or less.

15. The method of claim 11, wherein the concentration of the organic additive of interest in the plating bath is determined by implementing an electro-analytical technique selected from the group consisting of Modified Linear Approximation Technique (MLAT), Dilution Titration (DT), Response Curve (RC), and Quick Check (QC) techniques.

16. The method of claim 11, wherein the electrochemical response is selected from the group consisting of anodic stripping charge in milicoulombs, cathodic deposition charge in milicoulombs, anodic stripping rate, cathodic deposition rate, anodic stripping area, cathodic deposition area, differential electrical plating potential between cathodic and reference electrodes, electric current in milliampules, electrical potential in milivolts, AC current, DC current, and differential current.

17. The method of claim 11, wherein the electro-analytical principle is selected from the group consisting of Cyclic Voltammetric Stripping (CVS), Pulsed Cyclic Galvanostatic Analysis (PCGA), and Cyclic Pulsed Voltamic Stripping (CPVS).

18. The method of claim 11, wherein the method is applied to an acidic or basic metal plating bath and the metal to be plated is selected from the group consisting of copper, nickel, cobalt, silver, and combinations thereof.

19. An electro-analytical method for determining the concentration of an organic additive of interest in a plating bath, affecting the quality of a metal to be plated, using an organic chemical analyzer operating on the basis of an electro-analytical principle, comprising preparing a supporting-electrolyte solution, comprising a virgin make up solution of all inorganic substances of the plating bath and excess amounts of all other organic additives except the organic additive of interest;

preparing a testing solution, comprising the supporting-electrolyte solution and one or more volumes of a standard solution, wherein the standard solution comprises known concentration of one or more organic additives for the plating bath;

measuring an electrochemical response of the supporting-electrolyte solution and the testing solution using the organic chemical analyzer; and determining the concentration of the organic additive in the plating bath from the electrochemical response measurements.

20. The method of claim 19, wherein the concentration of an organic additive of interest selected from the group consisting of leveler, over-plate inhibitor, and grain refiner is determined independently of knowledge of the concentrations of an accelerator, suppressor, and other organic additive in the plating bath.

21. The method of claim 19, wherein the supporting-electrolyte solution, for determining the concentration of the organic additive of interest selected from the group consisting of leveler, over-plate inhibitor, and grain refiner, comprises the virgin make up solution, excess amounts of another organic additive selected from the group consisting of accelerator, brightener, and anti-suppressor, and excess amounts of another organic additive selected from the group consisting of suppressor, carrier, surfactant, and wetting agent.

22. The method of claim 21, wherein the excess amounts of all other organic additives in the supporting-electrolyte solution are at a concentration of about 60 ml/L or less.

23. The method of claim 19, wherein the concentration of the organic additive of interest in the plating bath is determined by implementing an electro-analytical technique selected from the group consisting of Modified Linear Approximation Technique (MLAT), Dilution Titration (DT), Response Curve (RC), and Quick Check (QC) techniques.

24. The method of claim 19, wherein the electrochemical response is selected from the group consisting of anodic stripping charge in milicoulombs, cathodic deposition charge in milicoulombs, anodic stripping rate, cathodic deposition rate, anodic stripping area, cathodic deposition area, differential electrical plating potential between cathodic and reference electrodes, electric current in milliampules, electrical potential in milivolts, AC current, DC current, and differential current.

25. The method of claim 19, wherein the electro-analytical principle is selected from the group consisting of Cyclic Voltammetric Stripping (CVS), Pulsed Cyclic Galvanostatic Analysis (PCGA), and Cyclic Pulsed Voltamic Stripping (CPVS).

26. The method of claim 19, wherein the method is applied to an acidic or basic metal plating bath and the metal to be plated is selected from the group consisting of copper, nickel, cobalt, silver, and combinations thereof.

27. An electro-analytical method for determining the concentration of an organic additive of interest selected from the group consisting of accelerator, brightener, and anti-suppressor, independently of knowledge of the concentration of a suppressing agent selected from the group consisting of suppressor, carrier, surfactant, wetting agent, leveler, over-plate inhibitor, grain refiner, and combinations thereof with minimal interference among organic additives in a plating bath using an organic chemical analyzer, comprising:

preparing a supporting-electrolyte solution, comprising a virgin make up solution, up to about 5 ml/L of the unknown organic additive of interest, and between about 10 ml/L and about 60 ml/L of the suppressing agent, wherein the virgin make up solution comprises at least three inorganic components selected from the group consisting of charged cations of the metal to be plated, charged anions, an acid or base for adjusting pH and bath electrical resistance, and combinations thereof;

preparing a testing solution, comprising the supporting-electrolyte solution and a production solution, wherein the production solution comprises a portion of the plating bath;

measuring an electrochemical response of the supporting-electrolyte solution and the testing solution using the organic chemical analyzer; and determining the concentration of the organic additive of interest in the plating bath from the electrochemical response measurements.

28. An electro-analytical method for determining the concentration of an organic additive of interest selected from the group consisting of suppressor, carrier, surfactant, and wetting agent, independently of knowledge of the concentration of an anti-suppressing agent selected from the group consisting of accelerator, brightener, anti-suppressor, leveler, over-plate inhibitor, grain refiner, and combinations thereof with minimal interference among organic additives in a plating bath using an organic chemical analyzer, comprising:

preparing a supporting-electrolyte solution, comprising a virgin make up solution of all inorganic substances of the plating bath and up to about 0.5 ml/L of the organic additive of interest, wherein the virgin make up solution comprises al least three inorganic components selected from the group consisting of charged cations of the metal to be plated, charged anions, an acid or base for adjusting pH and bath electrical resistance, and combinations thereof;

preparing a testing solution, comprising the supporting-electrolyte solution and one or more volumes of a standard solution, wherein the standard solution comprises known concentration of one or more organic additives for the plating bath;

measuring an electrochemical response of the supporting-electrolyte solution and the testing solution using the organic chemical analyzer; and determining the concentration of the organic additive of interest in the plating bath from the electrochemical response measurements.

29. An electro-analytical method for determining the concentration of an organic additive of interest selected from the group consisting of leveler, over-plate inhibitor, and grain refiner in a plating bath, independently of knowledge of the concentrations of any other suppressing and anti-suppressing agents from the plating bath with minimal interference among organic additives using an organic chemical analyzer, comprising:

preparing a supporting-electrolyte solution, comprising a virgin make up solution of all inorganic substances of the plating bath, up to about 60 ml/L of an anti-suppressing agent selected from the group consisting of accelerator, brightener, and anti-suppressor, and up to about 60 ml/L of a suppressing agent selected from the group consisting of suppressor, carrier, surfactant, and wetting agent, wherein the virgin make up solution comprises at least three inorganic components selected from the group consisting of positively charged cations of the metal to be plated, charged anions, an acid or base for adjusting pH and bath electrical resistance, and combinations thereof;

preparing a testing solution, comprising the supporting-electrolyte solution and one or more volumes of a standard solution, wherein the standard solution comprises known concentration of one or more organic additives for the plating bath;

measuring an electrochemical response of the supporting-electrolyte solution using the organic chemical analyzer; and determining the concentration of the organic additive of interest in the plating bath from the electrochemical response measurements.

30. A method for analyzing an electrolyte in a electrochemical deposition system having one or more process cells in communication with a main electrolyte supply tank, comprising:

flowing at least a portion of the electrolyte from the main electrolyte supply tank to one or more chemical analyzers; and analyzing the concentrations of inorganic additives and organic additives in the electrolyte from the electrochemical deposition system, wherein analyzing the concentration of an organic additive of interest further comprises:

preparing a supporting-electrolyte solution, comprising a virgin make up solution of all inorganic additives of the electrolyte, up to about 5 ml/L of the organic additive of interest, and between about 10 ml/L and about 60 ml/L of a suppressing agent from the electrolyte, wherein the virgin make up solution comprises at least three inorganic components selected from the group consisting of charged cations of the metal to be plated, charged anions, an acid or base for adjusting pH and bath electrical resistance, and combinations thereof;

preparing a testing solution, comprising the supporting-electrolyte solution and a production solution, wherein the production solution comprises a portion of the electrolyte;

measuring an electrochemical response of the supporting-electrolyte solution and the testing solution using one of the chemical analyzers; and determining the concentration of the organic additive of interest in the electrolyte from the electrochemical response measurements.

31. A method for analyzing an electrolyte in a electrochemical deposition system having one or more process cells in communication with a main electrolyte supply tank, comprising:

flowing at least a portion of the electrolyte from the main electrolyte supply tank to one or more chemical analyzers; and analyzing the concentrations of inorganic additives and organic additives in the electrolyte from the electrochemical deposition system, wherein analyzing the concentration of an organic additive of interest further comprises:

preparing a supporting-electrolyte solution, comprising a virgin make up solution of all inorganic additives of the electrolyte and up to about 0.5 ml/L of the organic additive of interest, wherein the virgin make up solution comprises at least three inorganic components selected from the group consisting of charged cations of the metal to be plated, charged anions, an acid or base for adjusting pH and bath electrical resistance, and combinations thereof;

preparing a testing solution, comprising the supporting-electrolyte solution and one or more volumes of a standard solution, wherein the standard solution comprises known concentration of one or more organic additives for the electrolyte;

measuring an electrochemical response of the supporting-electrolyte solution and the testing solution using one of the chemical analyzers; and determining the concentration of the organic additive of interest in the electrolyte from the electrochemical response measurements.

32. A method for analyzing an electrolyte in a electrochemical deposition system having one or more process cells in communication with a main electrolyte supply tank, comprising:

flowing at least a portion of the electrolyte from the main electrolyte supply tank to one or more chemical analyzers; and analyzing the concentrations of inorganic additives and organic additives in the electrolyte from the electrochemical deposition system, wherein analyzing the concentration of an organic additive of interest further comprises:

preparing a supporting-electrolyte solution, comprising a virgin make up solution of all inorganic additives of the plating bath and up to about 60 ml/L of all other organic additives except the organic additive of interest, wherein the virgin make up solution comprises at least three inorganic components selected from the group consisting of charged cations of the metal to be plated, charged anions, an acid or base for adjusting pH and bath electrical resistance, and combinations thereof;

preparing a testing solution, comprising the supporting-electrolyte solution and one or more volumes of a standard solution, wherein the standard solution comprises known concentration of one or more organic additives for the electrolyte;

measuring an electrochemical response of the supporting-electrolyte solution and the testing solution using one of the chemical analyzers; and determining the concentration of the organic additive of interest in the electrolyte from the electrochemical response measurements.

33. An electrochemical deposition system, comprising:

an electrolyte supply tank containing an electrolyte in fluid communication with one or more electrochemical process cells;

a chemical analyzer module comprising one or more chemical analyzers in communication with the electrolyte supply tank, wherein the one or more chemical analyzers comprise an organic chemical analyzer and an inorganic chemical analyzer; and a controller coupled to the one or more chemical analyzers to determine the concentrations of inorganic additives and organic additives in the electrolyte, wherein analyzing the concentrations of an organic additive of interest in the electrolyte by the controller further comprises:

preparing a supporting-electrolyte solution, comprising a virgin make up solution of all inorganic additives of the electrolyte, up to about 5 ml/L of the organic additive of interest, and between about 10 ml/L and about 60 ml/L of a suppressing agent from the electrolyte, wherein the virgin make up solution comprises at least three inorganic components selected from the group consisting of charged cations of the metal to be plated, charged anions, an acid or base for adjusting pH and bath electrical resistance, and combinations thereof;

preparing a testing solution, comprising the supporting-electrolyte solution and a production solution, wherein the production solution comprises a portion of the electrolyte;

measuring an electrochemical response of the supporting-electrolyte solution and the testing solution using the organic chemical analyzer; and determining the concentration of the organic additive of interest in the electrolyte from the electrochemical response measurements.

34. An electrochemical deposition system, comprising:

an electrolyte supply tank containing an electrolyte in fluid communication with one or more electrochemical process cells;

a chemical analyzer module comprising one or more chemical analyzers in communication with the electrolyte supply tank, wherein the one or more chemical analyzers comprise an organic chemical analyzer and an inorganic chemical analyzer; and a controller coupled to the one or more chemical analyzers to determine the concentrations of inorganic additives and organic additives in the electrolyte, wherein analyzing the concentrations of an organic additive of interest in the electrolyte by the controller further comprises:

preparing a supporting-electrolyte solution, comprising a virgin make up solution of all inorganic additives of the plating bath and up to about 0.5 ml/L of the organic additive of interest, wherein the virgin make up solution comprises at least three inorganic components selected from the group consisting of charged cations of the metal to be plated, charged anions, an acid or base for adjusting pH and bath electrical resistance, and combinations thereof;

preparing a testing solution, comprising the supporting-electrolyte solution and one or more volumes of a standard solution, wherein the standard solution comprises known concentration of one or more organic additives for the electrolyte;

measuring an electrochemical response of the supporting-electrolyte solution and the testing solution using the organic chemical analyzer; and determining the concentration of the organic additive of interest in the electrolyte from the electrochemical response measurements.

35. An electro-chemical deposition system, comprising:

an electrolyte supply tank containing an electrolyte in fluid communication with one or more electrochemical process cells;

a chemical analyzer module comprising one or more chemical analyzers in communication with the electrolyte supply tank, wherein the one or more chemical analyzers comprise an organic chemical analyzer and an inorganic chemical analyzer; and a controller coupled to the one or more chemical analyzers to determine the concentrations of inorganic additives and organic additives in the electrolyte, wherein analyzing the concentrations of an organic additive of interest in the electrolyte by the controller further comprises:

preparing a supporting-electrolyte solution, comprising a virgin make up solution of all inorganic additives of the plating bath and up to about 60 ml/L of all other organic additives except the organic additive of interest, wherein the virgin make up solution comprises at least three inorganic components selected from the group consisting of charged cations of the metal to be plated, charged anions, an acid or base for adjusting pH and bath electrical resistance, and combinations thereof;

preparing a testing solution, comprising the supporting-electrolyte solution and one or more volumes of a standard solution, wherein the standard solution comprises known concentration of one or more organic additives for the electrolyte;

measuring an electrochemical response of the supporting-electrolyte solution and the testing solution using the organic chemical analyzer; and determining the concentration of the organic additive of interest in the electrolyte from the electrochemical response measurements.

* * * * *

UNITED STATES PATENT AND TRADEMARK OFFICE
Certificate

Patent No. 6,808,611 B2                            Patented: October 26, 2004

ON petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Zhi-wen Sun, San Jose, CA (US); Chunman Yu, Sunnyvale, CA (US); Brian Metzger, Bozeman, MT (US); David W. Nguyen, San Jose, CA (US); Girish Dixit, San Jose, CA (US); Peter Bratin, Flushing, NY (NY); Michael Pavlov, Fairlawn, NJ (US); and Eugene Shalyt, Washington Township, NJ (US).

Signed and Sealed this Twelfth Day of July 2011.

MICHAEL MARCHESCHI
*Supervisory Patent Examiner*
Art Unit 1775
Tecnology Center 1700